_(12)_ United States Patent
Dachs, II et al.

(10) Patent No.: US 10,912,616 B2
(45) Date of Patent: Feb. 9, 2021

(54) COUPLER TO TRANSFER MOTION TO SURGICAL INSTRUMENT FROM TELEOPERATED ACTUATOR

(71) Applicant: Intuitive Surgical Operations, Inc., Sunnyvale, CA (US)

(72) Inventors: Gregory W. Dachs, II, San Mateo, CA (US); Bruce Michael Schena, Menlo Park, CA (US); Amir Chaghajerdi, San Jose, CA (US); Niels Smaby, Palo Alto, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1120 days.

(21) Appl. No.: 15/121,374

(22) PCT Filed: Mar. 17, 2015

(86) PCT No.: PCT/US2015/020884
§ 371 (c)(1),
(2) Date: Aug. 24, 2016

(87) PCT Pub. No.: WO2015/142791
PCT Pub. Date: Sep. 24, 2015

(65) Prior Publication Data
US 2016/0361131 A1    Dec. 15, 2016

Related U.S. Application Data

(60) Provisional application No. 61/954,571, filed on Mar. 17, 2014, provisional application No. 61/954,557, (Continued)

(51) Int. Cl.
*A61B 34/30* (2016.01)
*A61B 17/00* (2006.01)
*A61B 90/00* (2016.01)

(52) U.S. Cl.
CPC .... *A61B 34/30* (2016.02); *A61B 2017/00477* (2013.01); *A61B 2090/0813* (2016.02)

(58) Field of Classification Search
CPC ....... A61B 34/30; A61B 34/35; F16B 21/071; F16B 21/073; F16B 21/079
See application file for complete search history.

(56) References Cited

U.S. PATENT DOCUMENTS

| | | |
|---|---|---|
| 4,542,272 A | 9/1985 | Hubbard et al. |
| 5,214,573 A | 5/1993 | Roza |

(Continued)

FOREIGN PATENT DOCUMENTS

| | | |
|---|---|---|
| CN | 101297267 A | 10/2008 |
| CN | 101443162 A | 5/2009 |

(Continued)

OTHER PUBLICATIONS

Extended European Search Report for Application No. EP15764610. 0, dated Nov. 23, 2017, 8 pages.

(Continued)

*Primary Examiner* — Daniel J Wiley
(74) *Attorney, Agent, or Firm* — Jones Robb, PLLC

(57) ABSTRACT

A sterile adapter for coupling a surgical instrument and a surgical instrument manipulator includes a bottom component and a coupling component. The bottom component includes a bottom component opening with a bottom lip having a locking mechanism. The coupling component is rotatably coupled to the bottom component. The coupling component includes an engagement feature that engages the surgical instrument manipulator. The coupling component further includes a locking mechanism opening that engages the locking mechanism when the engagement feature has not engaged the surgical instrument manipulator. The coupling component may include a retention tab that is aligned with (Continued)

the keyway to insert the coupling component into the bottom component opening and then misaligned with the keyway to retain the coupling component in the bottom component opening. A ramp may be provided on a leading edge of a pocket to facilitate engaging the coupling component with the surgical instrument manipulator.

12 Claims, 12 Drawing Sheets

Related U.S. Application Data filed on Mar. 17, 2014, provisional application No. 61/954,497, filed on Mar. 17, 2014, provisional application No. 61/954,502, filed on Mar. 17, 2014, provisional application No. 61/954,595, filed on Mar. 17, 2014, provisional application No. 62/019,318, filed on Jun. 30, 2014, provisional application No. 62/103,991, filed on Jan. 15, 2015, provisional application No. 62/104,306, filed on Jan. 16, 2015.

(56) References Cited

U.S. PATENT DOCUMENTS

| | | | |
|---|---|---|---|
| 5,679,423 | A | 10/1997 | Shah |
| 5,803,086 | A | 9/1998 | Scholz et al. |
| 6,331,181 | B1 | 12/2001 | Tierney et al. |
| 6,471,172 | B1 | 10/2002 | Lemke et al. |
| 7,096,870 | B2 | 8/2006 | Lamprich et al. |
| 7,125,403 | B2 | 10/2006 | Julian et al. |
| 7,758,569 | B2 | 7/2010 | Brock |
| 7,947,050 | B2 | 5/2011 | Lee et al. |
| 7,963,913 | B2 | 6/2011 | Devengenzo et al. |
| 8,220,468 | B2 | 7/2012 | Cooper et al. |
| 8,506,555 | B2 | 8/2013 | Ruiz |
| 8,529,582 | B2 | 9/2013 | Devengenzo et al. |
| 8,555,892 | B2 | 10/2013 | Traub |
| 8,998,930 | B2 * | 4/2015 | Orban, III ............... A61B 34/30 606/130 |
| 9,687,312 | B2 | 6/2017 | Dachs, II et al. |
| 9,839,487 | B2 | 12/2017 | Dachs, II et al. |
| 10,022,193 | B2 | 7/2018 | Cooper et al. |
| 10,045,828 | B2 | 8/2018 | Dachs, II et al. |
| 10,213,268 | B2 | 2/2019 | Dachs, Ii |
| 10,278,784 | B2 | 5/2019 | Dachs, Ii |
| 10,363,109 | B2 | 7/2019 | Dachs, II et al. |
| 10,420,622 | B2 | 9/2019 | Dachs et al. |
| 10,485,621 | B2 | 11/2019 | Morrissette et al. |
| 10,537,400 | B2 | 1/2020 | Dachs, Ii et al. |
| 10,543,051 | B2 | 1/2020 | Schena et al. |
| 10,595,836 | B2 | 3/2020 | Smaby et al. |
| 10,610,320 | B2 | 4/2020 | Dachs, II et al. |
| 10,639,119 | B2 | 5/2020 | Dachs, Ii et al. |
| 2002/0032452 | A1 | 3/2002 | Tierney et al. |
| 2002/0111635 | A1 | 8/2002 | Jensen et al. |
| 2003/0216723 | A1 | 11/2003 | Shinmura et al. |
| 2004/0049205 | A1 | 3/2004 | Lee et al. |
| 2005/0240178 | A1 | 10/2005 | Morley et al. |
| 2005/0244217 | A1 | 11/2005 | Burke et al. |
| 2006/0235436 | A1 | 10/2006 | Anderson et al. |
| 2006/0260622 | A1 | 11/2006 | Wooley et al. |
| 2007/0119274 | A1 | 5/2007 | Devengenzo et al. |
| 2007/0142971 | A1 | 6/2007 | Schena et al. |
| 2008/0103491 | A1 | 5/2008 | Omori et al. |
| 2008/0140088 | A1 | 6/2008 | Orban, III |
| 2010/0163057 | A1 | 7/2010 | Anderson et al. |
| 2010/0170519 | A1 | 7/2010 | Romo et al. |
| 2010/0175701 | A1 | 7/2010 | Reis et al. |
| 2010/0234857 | A1 | 9/2010 | Itkowitz et al. |
| 2011/0015650 | A1 | 1/2011 | Choi et al. |
| 2011/0084113 | A1 | 4/2011 | Bedi et al. |
| 2011/0118754 | A1 | 5/2011 | Dachs, II et al. |
| 2011/0213383 | A1 | 9/2011 | Lee et al. |
| 2011/0277776 | A1 | 11/2011 | McGrogan et al. |
| 2011/0288560 | A1 | 11/2011 | Shohat et al. |
| 2011/0290854 | A1 | 12/2011 | Timm et al. |
| 2011/0290855 | A1 | 12/2011 | Moore et al. |
| 2011/0295270 | A1 | 12/2011 | Giordano et al. |
| 2011/0313477 | A1 | 12/2011 | McLean et al. |
| 2012/0197094 | A1 | 8/2012 | Zhang et al. |
| 2012/0239060 | A1 | 9/2012 | Orban, III |
| 2012/0247489 | A1 | 10/2012 | Orban, III et al. |
| 2012/0292367 | A1 | 11/2012 | Morgan et al. |
| 2013/0110129 | A1 | 5/2013 | Reid et al. |
| 2013/0211397 | A1 | 8/2013 | Parihar et al. |
| 2013/0211401 | A1 | 8/2013 | Bailey et al. |
| 2013/0274062 | A1 | 10/2013 | Arai et al. |
| 2013/0274657 | A1 | 10/2013 | Zirps et al. |
| 2013/0325034 | A1 | 12/2013 | Schena et al. |
| 2013/0331858 | A1 | 12/2013 | Devengenzo et al. |
| 2014/0001234 | A1 | 1/2014 | Shelton, IV et al. |
| 2014/0066944 | A1 | 3/2014 | Taylor et al. |
| 2014/0069437 | A1 | 3/2014 | Reis et al. |
| 2015/0223832 | A1 | 8/2015 | Swaney et al. |
| 2015/0257841 | A1 | 9/2015 | Dachs, II |
| 2015/0257842 | A1 | 9/2015 | Dachs, II |
| 2016/0184037 | A1 | 6/2016 | Cooper et al. |
| 2016/0354173 | A1 | 12/2016 | Dachs, II et al. |
| 2016/0361049 | A1 | 12/2016 | Dachs, II et al. |
| 2016/0361124 | A1 | 12/2016 | Dachs, II et al. |
| 2016/0361126 | A1 | 12/2016 | Schena et al. |
| 2016/0361127 | A1 | 12/2016 | Dachs, II et al. |
| 2016/0361129 | A1 | 12/2016 | Morrissette et al. |
| 2016/0367328 | A1 | 12/2016 | Dachs, II et al. |
| 2017/0172549 | A1 | 6/2017 | Smaby et al. |
| 2017/0273752 | A1 | 9/2017 | Dachs, II et al. |
| 2018/0064501 | A1 | 3/2018 | Dachs, II |
| 2018/0168752 | A1 | 6/2018 | Scheib et al. |
| 2018/0344419 | A1 | 12/2018 | Dachs, II et al. |
| 2019/0183596 | A1 | 6/2019 | Dachs, II |
| 2019/0254766 | A1 | 8/2019 | Dachs, II |
| 2019/0365494 | A1 | 12/2019 | Dachs, II et al. |
| 2019/0380803 | A1 | 12/2019 | Dachs, II et al. |
| 2020/0069389 | A1 | 3/2020 | Morrissette et al. |
| 2020/0155130 | A1 | 5/2020 | Smaby et al. |

FOREIGN PATENT DOCUMENTS

| | | |
|---|---|---|
| CN | 102630154 A | 8/2012 |
| DE | 102012008535 A1 | 10/2013 |
| DE | 102012013242 A1 | 1/2014 |
| EP | 1862123 A2 | 12/2007 |
| EP | 2259744 A1 | 12/2010 |
| GB | 2538326 A | 11/2016 |
| JP | H0666326 A | 3/1994 |
| JP | 2001187067 A | 7/2001 |
| JP | 2012210294 A | 11/2012 |
| JP | 2013034859 A | 2/2013 |
| KR | 20110032444 A | 3/2011 |
| KR | 20110036452 A | 4/2011 |
| KR | 20110095795 A | 8/2011 |
| KR | 20130080638 A | 7/2013 |
| KR | 20130120316 A | 11/2013 |
| WO | WO-2007075864 A1 | 7/2007 |
| WO | WO-2007095637 A1 | 8/2007 |
| WO | WO-2007126443 A2 | 11/2007 |
| WO | WO-2009151205 A1 | 12/2009 |
| WO | WO-2010126128 A1 | 11/2010 |
| WO | WO-2011037394 A2 | 3/2011 |
| WO | WO-2011143016 A1 | 11/2011 |
| WO | WO-2013018931 A1 | 2/2013 |
| WO | WO-2013181536 A1 | 12/2013 |
| WO | WO-2014035803 A1 | 3/2014 |
| WO | WO-2015023730 A1 | 2/2015 |
| WO | WO-2015142824 A1 | 9/2015 |

OTHER PUBLICATIONS

Extended European Search Report for Application No. EP15764881. 7, dated Nov. 30, 2017, 10 pages.

(56) References Cited

OTHER PUBLICATIONS

Extended European Search Report for Application No. 15766019.2, dated Oct. 20, 2017, 7 pages.
Extended European Search Report for Application No. 15765493.0, dated Jul. 28, 2017, 7 pages.
Extended European Search Report for Application No. 15765779.2, dated Jul. 18, 2017, 8 pages.
Extended European Search Report for Application No. EP15764089.7, dated Oct. 25, 2017, 11 pages.
Extended European Search Report for Application No. EP15764268.7, dated Nov. 6, 2017, 8 pages.
Extended European Search Report for Application No. EP15764745.4, dated Oct. 30, 2017, 10 pages.
Extended European Search Report for Application No. EP15764940.1, dated Oct. 30, 2017, 8 pages.
Extended European Search Report for Application No. EP19201778.8, dated Nov. 27, 2019, 5 pages.
Extended European Search Report for Application No. EP20154204.0, dated May 7, 2020, 7 pages.
Extended European Search Report for Application No. EP20154737.9, dated Apr. 17, 2020, 10 pages.
Extended European Search Report for Application No. EP20161337.9, dated May 7, 2020, 8 pages.
International Search Report and Written Opinion for Application No. PCT/US15/21111, dated May 21, 2015, 10 pages.
International Search Report and Written Opinion for Application No. PCT/US15/20880, dated Jul. 14, 2015, 9 pages.
International Search Report and Written Opinion for Application No. PCT/US15/20882, dated May 29, 2015, 14 pages.
International Search Report and Written Opinion for Application No. PCT/US15/20884, dated Jun. 12, 2015, 13 pages.
International Search Report and Written Opinion for Application No. PCT/US15/20886, dated Jun. 4, 2015, 19 pages.
International Search Report and Written Opinion for Application No. PCT/US15/20876, dated Jun. 12, 2015, 17 pages.
International Search Report and Written Opinion for Application No. PCT/US15/20885, dated Jun. 5, 2015, 7 pages.
International Search Report and Written Opinion for Application No. PCT/US15/20888, dated Jun. 5, 2015, 9 pages.
International Search Report and Written Opinion for Application No. PCT/US15/21020, dated Jun. 5, 2015, 10 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP20159147.6, dated Jun. 16. 2020, 7 pages.
Extended European Search Report for Application No. 19181058.9 dated Aug. 22, 2019, 7 pages.

\* cited by examiner

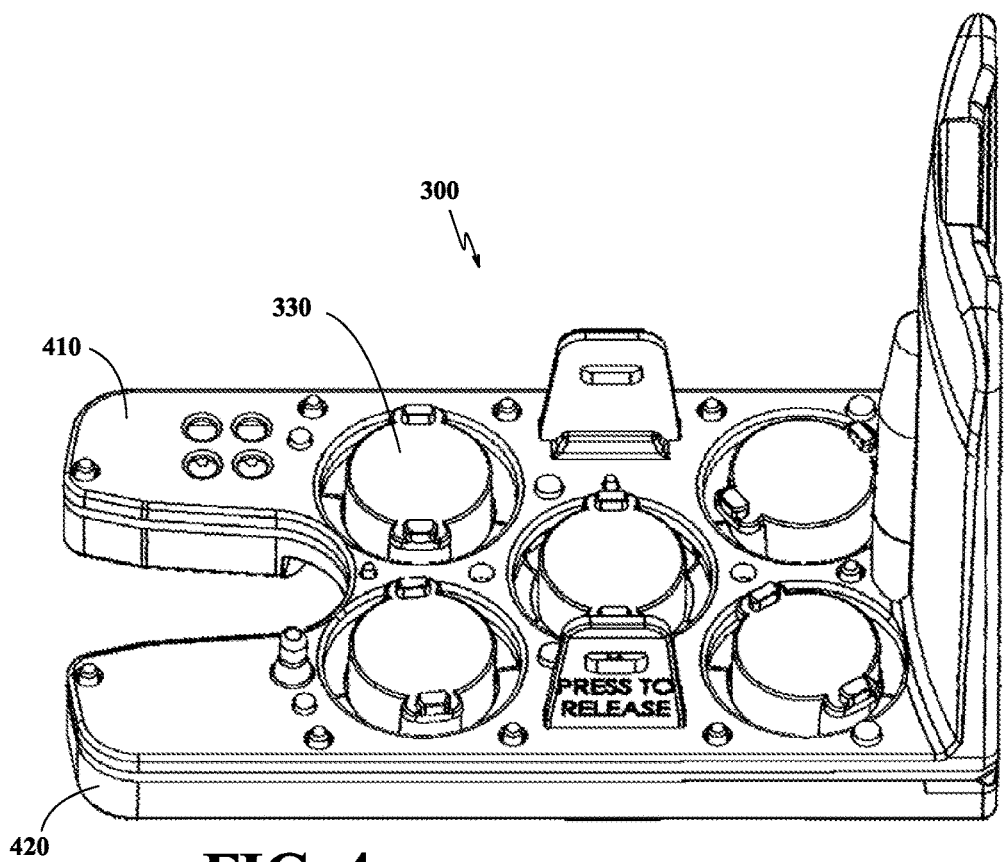
FIG. 4
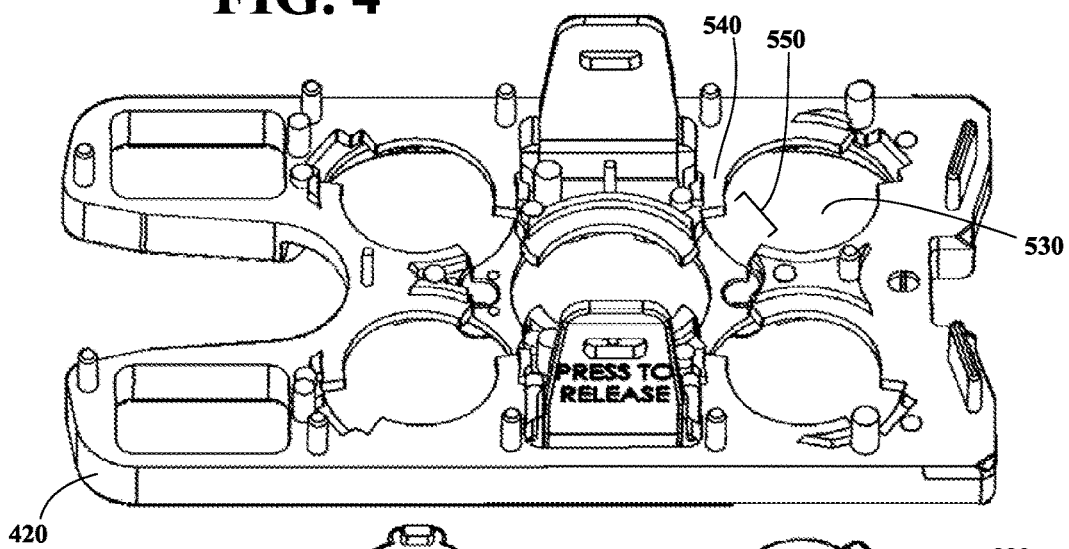
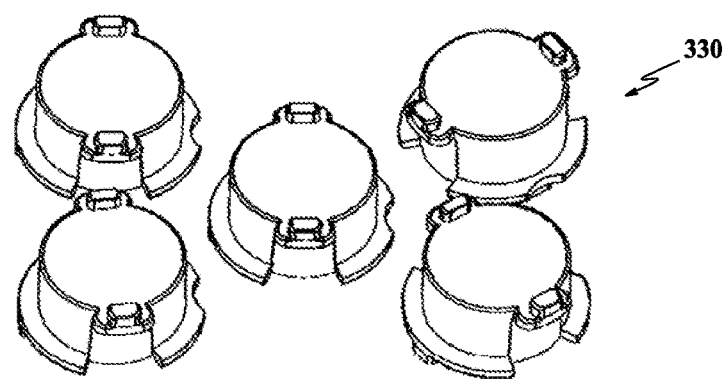
FIG. 5

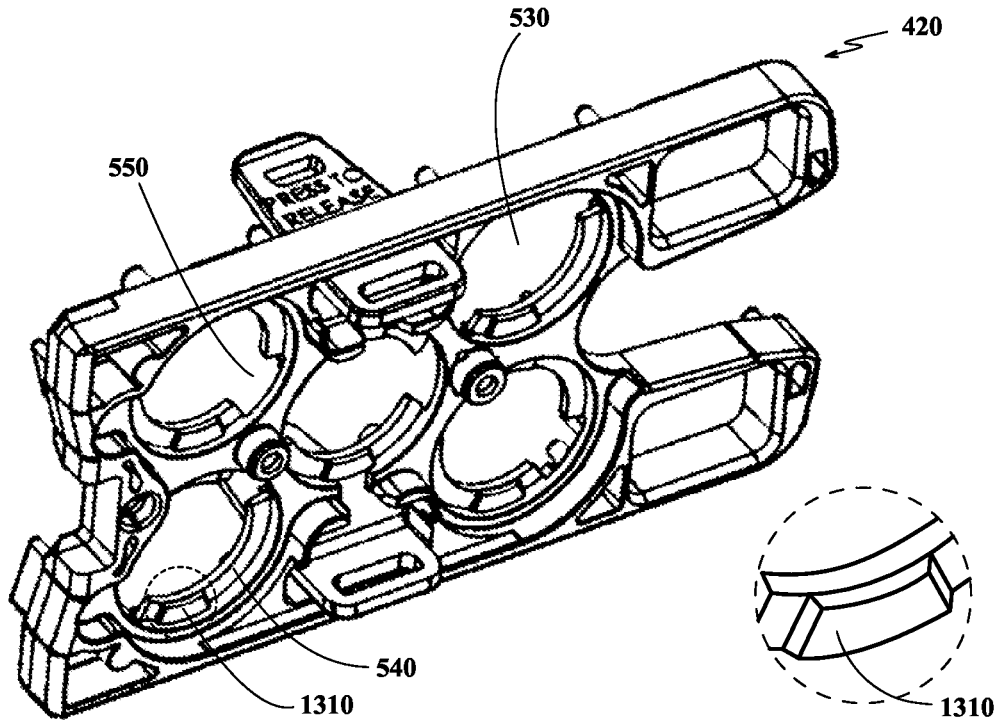
FIG. 13A  FIG. 13B
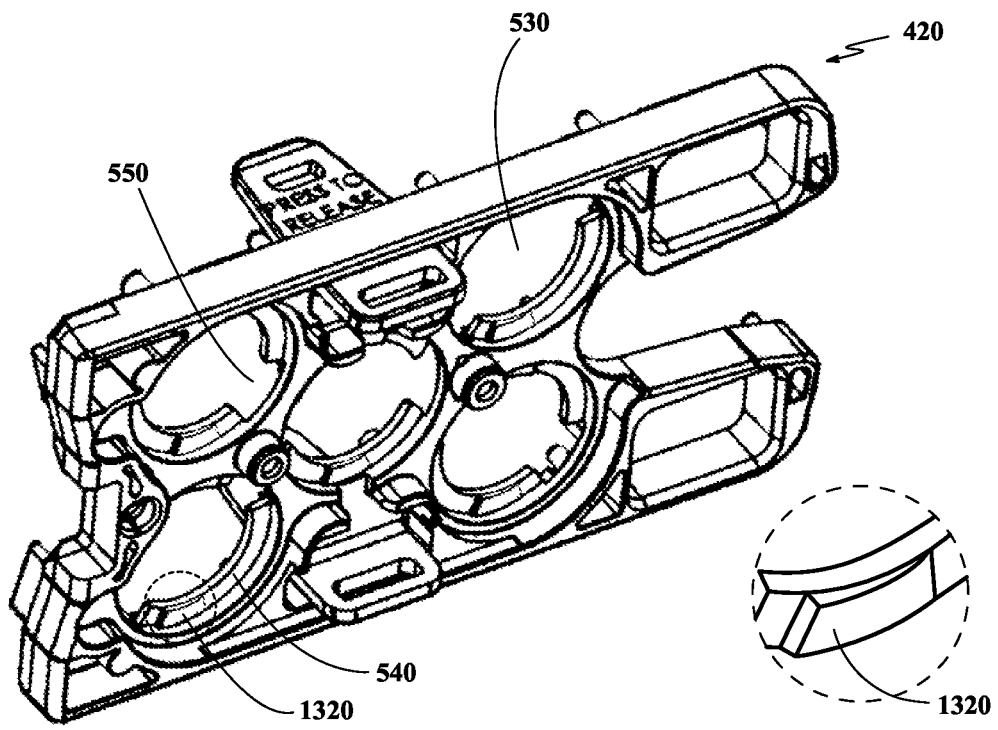
FIG. 13C  FIG. 13D

COUPLER TO TRANSFER MOTION TO SURGICAL INSTRUMENT FROM TELEOPERATED ACTUATOR

This application is a 371 of international application number PCT/US15/020884 filed Mar. 17, 2015, and claims benefit of the following earlier filed applications:

| | |
|---|---|
| U.S. Pat. No. 61/954,497 | 17 Mar. 2014 (17-03-2014) |
| U.S. Pat. No. 61/954,502 | 17 Mar. 2014 (17-03-2014) |
| U.S. Pat. No. 61/954,557 | 17 Mar. 2014 (17-03-2014) |
| U.S. Pat. No. 61/954,571 | 17 Mar. 2014 (17-03-2014) |
| U.S. Pat. No. 61/954,595 | 17 Mar. 2014 (17-03-2014) |
| U.S. Pat. No. 62/019,318 | 30 Jun. 2014 (30-06-2014) |
| U.S. Pat. No. 62/103,991 | 15 Jan. 2015 (15-01-2015) |
| U.S. Pat. No. 62/104,306 | 16 Jan. 2015 (16-01-2015) |

Each of these applications is specifically incorporated herein by reference to the greatest extent permitted.

FIELD

Embodiments of the invention relate to the field of field of mechanical couplers; and more specifically, to a mechanical coupler for transferring motion from a teleoperated actuator to an attached surgical instrument.

BACKGROUND

Minimally invasive medical techniques have been used to reduce the amount of extraneous tissue which may be damaged during diagnostic or surgical procedures, thereby reducing patient recovery time, discomfort, and deleterious side effects. Traditional forms of minimally invasive surgery include endoscopy. One of the more common forms of endoscopy is laparoscopy, which is minimally invasive inspection or surgery within the abdominal cavity. In traditional laparoscopic surgery, a patient's abdominal cavity is insufflated with gas, and cannula sleeves are passed through small (approximately 12 mm) incisions in the musculature of the patient's abdomen to provide entry ports through which laparoscopic surgical instruments can be passed in a sealed fashion.

The laparoscopic surgical instruments generally include a laparoscope for viewing the surgical field and surgical instruments having end effectors. Typical surgical end effectors include clamps, graspers, scissors, staplers, and needle holders, for example. The surgical instruments are similar to those used in conventional (open) surgery, except that the working end or end effector of each surgical instrument is separated from its handle by an approximately 30 cm. long extension tube, for example, so as to permit the operator to introduce the end effector to the surgical site and to control movement of the end effector relative to the surgical site from outside a patient's body.

In order to provide improved control of the working tools, it may be desirable to control the surgical instrument with teleoperated actuators. The surgeon may operate controls on a console to indirectly manipulate the instrument that is connected to the teleoperated actuators. The surgical instrument is detachably coupled to the teleoperated actuators so that the surgical instrument can be separately sterilized and selected for use as needed instrument for the surgical procedure to be performed. The surgical instrument may be changed during the course of a surgery.

Performing surgery with teleoperated surgical instruments creates new challenges. One challenge is the need to maintain the region adjacent the patient in a sterile condition. However, the motors, sensors, encoders and electrical connections that are necessary to control the surgical instruments typically cannot be sterilized using conventional methods, e.g., steam, heat and pressure or chemicals, because they would be damaged or destroyed in the sterilization process.

Another challenge with teleoperated surgery systems is that a surgeon will typically employ several different surgical instruments during a procedure. A number of different surgical instruments will typically be introduced through the same trocar sleeve during the operation to limit the number of incisions required. Thus, there are a limited number of instrument holders available, often fewer than the number of surgical instruments used during a procedure. Therefore the surgical instruments may be attached and detached from the same instrument holder a number of times during an operation. A number of connections are required between the surgical instrument and the teleoperated actuator and its controller. Connections are required to transmit the actuator forces, electrical signals, and data. This makes the attachment of the surgical instrument to the teleoperated actuator and its controller complex.

Still another challenge with teleoperated surgery systems is that an operating room is not an ideal environment for preparing precision mechanical assemblies.

It would be desirable to provide an easier and more effective way to engage and disengage a surgical instrument and a teleoperated actuator drive while preventing contamination of the teleoperated actuator and allowing quick and reliable attachment of a succession of surgical instruments that maintains a sterile area around the surgical instrument.

It would be desirable to provide an easier and more effective way to engage and disengage a surgical instrument and a teleoperated actuator drive while preventing contamination of the teleoperated actuator and allowing quick and reliable attachment of a succession of surgical instruments that maintains a sterile area around the surgical instrument.

SUMMARY

A sterile adapter for coupling a surgical instrument and a surgical instrument manipulator includes a bottom component and a coupling component. The bottom component includes a bottom component opening with a bottom lip having a locking mechanism. The coupling component is rotatably coupled to the bottom component. The coupling component includes an engagement feature that engages the surgical instrument manipulator. The coupling component further includes a locking mechanism opening that engages the locking mechanism when the engagement feature has not engaged the surgical instrument manipulator. The coupling component may include a retention tab that is aligned with the keyway to insert the coupling component into the bottom component opening and then misaligned with the keyway to retain the coupling component in the bottom component opening. A ramp may be provided on a leading edge of a pocket to facilitate engaging the coupling component with the surgical instrument manipulator.

Other features and advantages of the present invention will be apparent from the accompanying drawings and from the detailed description that follows below.

BRIEF DESCRIPTION OF THE DRAWINGS

The invention may best be understood by referring to the following description and accompanying drawings that are used to illustrate embodiments of the invention by way of example and not limitation. In the drawings, in which like reference numerals indicate similar elements:

FIG. 4 is an illustration of an exemplary embodiment of an assembled ISA.

FIG. 5 is an illustration of an ISA bottom component and a plurality of ISA couplers.

FIG. 13A is an illustration of an exemplary embodiment of an ISA bottom component having a locking mechanism illustrated as a boss.

FIG. 13B is an enlarged illustration of the boss locking mechanism illustrated in a portion of FIG. 13A.

FIG. 13C is an illustration of an exemplary embodiment of an ISA bottom component having a locking mechanism illustrated as a ratchet.

FIG. 13D is an enlarged illustration of the ratchet locking mechanism illustrated in a portion of FIG. 13C.

DESCRIPTION OF EMBODIMENTS

Figure 1:
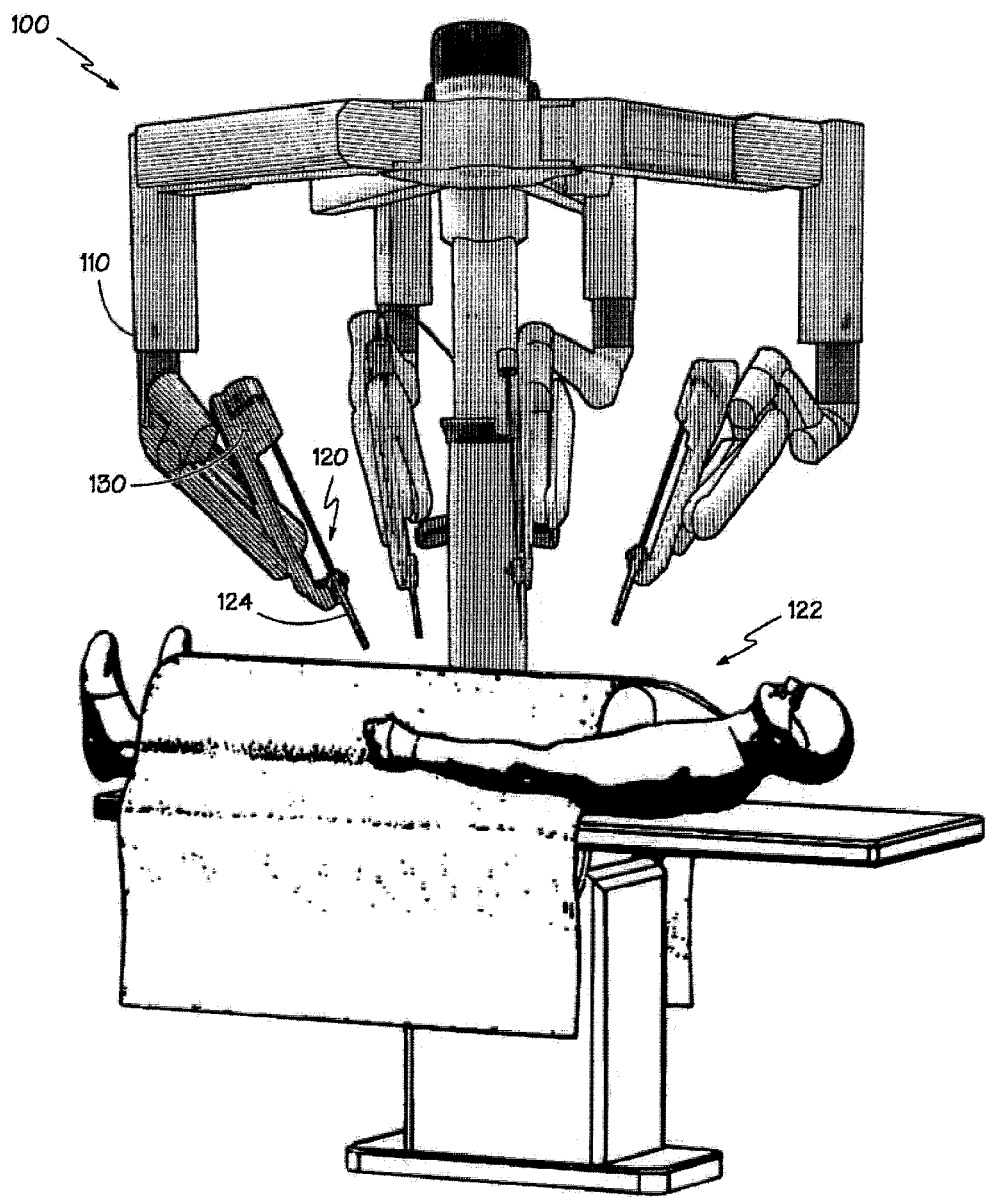
FIG. 1 is a view of an illustrative patient-side portion of a teleoperated surgical system.

In the following description, numerous specific details are set forth. However, it is understood that embodiments of the invention may be practiced without these specific details. In other instances, well-known circuits, structures, and techniques have not been shown in detail in order not to obscure the understanding of this description.

In the following description, reference is made to the accompanying drawings, which illustrate several embodiments of the present invention. It is understood that other embodiments may be utilized, and mechanical compositional, structural, electrical, and operational changes may be made without departing from the spirit and scope of the present disclosure. The following detailed description is not to be taken in a limiting sense, and the scope of the embodiments of the present invention is defined only by the claims of the issued patent.

The terminology used herein is for the purpose of describing particular embodiments only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

The term "object" generally refers to a component or group of components. For example, an object may refer to either a pocket or a boss of a disk within the specification or claims. Throughout the specification and claims, the terms "object," "component," "portion," "part" and "piece" are used interchangeably.

The terms "instrument" and "surgical instrument "are used herein to describe a medical device configured to be inserted into a patient's body and used to carry out surgical or diagnostic procedures. The instrument includes an end effector. The end effector may be a surgical tool associated with one or more surgical tasks, such as a forceps, a needle driver, a shears, a bipolar cauterizer, a tissue stabilizer or retractor, a clip applier, an anastomosis device, an imaging device (e.g., an endoscope or ultrasound probe), and the like. Some instruments used with embodiments of the invention further provide an articulated support (sometimes referred to as a "wrist") for the surgical tool so that the position and orientation of the surgical tool can be manipulated with one or more mechanical degrees of freedom in relation to the instrument's shaft. Further, many surgical end effectors include a functional mechanical degree of freedom, such as jaws that open or close, or a knife that translates along a path. Surgical instruments may also contain stored (e.g., on a semiconductor memory inside the instrument) information that may be permanent or may be updatable by the surgical system. Accordingly, the system may provide for either one-way or two-way information communication between the instrument and one or more system components.

The term "pocket" may be construed broadly as a recess of a workspace which is configured such that a boss is able to mate with the pocket. Such a mating process occurs when a boss of the appropriate shape and size is inserted into the pocket.

The term "boss" may be construed broadly as an extending or protruding feature on a workspace. A boss may be configured as any shape or size. One use of a boss is to participate in a mating process with a pocket through insertion of the boss into the pocket. Throughout the specification, the terms "boss" and "protrusion" are used interchangeably.

The term "engagement feature" may be construed broadly as a "pocket" or a "boss" or any piece used to engage two or more objects.

The term "mating" may be construed broadly as any event in which two or more objects are connected in a manner allowing the mated objects to operate in conjunction with one another. It should be noted that mating does not require a direct connection (e.g., direct physical or electrical connection) but that a multiplicity of objects or components may be used to mate two or more objects. For example, objects A and B may be mated through the use of object C. As another example, objects D and E may mate when object D, a protrusion, is received into the recess of object E, a pocket. Throughout the specification and claims, the terms "mate," "couple," "connect" or "engage" are used interchangeably.

In addition, the term "detachably coupled" or "detachably mated" may be construed to mean a coupling or mating event between two or more objects that is not permanent. This means that objects that are detachably coupled may be uncoupled and separated such that they no longer operate in conjunction.

The term "backlash" may be construed as the clearance or gap between two mated components. For instance, when a boss is inserted into a pocket, the protrusion of the boss is inherently smaller than opening of the pocket. The difference between the size of the protrusion and the size of the opening is the amount of backlash between the boss and the pocket.

Lastly, the terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

Overview of a Functional Teleoperated Surgical System

FIG. 1 is a view of an illustrative patient-side portion 100 of a teleoperated surgical system, in accordance with embodiments of the present invention. The patient-side portion 100 includes support assemblies 110 and one or more surgical instrument manipulators 112 at the end of each support assembly. The support assemblies optionally include one or more unpowered, lockable setup joints that are used to position the surgical instrument manipulator(s) 112 with reference to the patient for surgery. As depicted, the patient-side portion 100 rests on the floor. In other embodiments the patient-side portion may be mounted to a wall, to the ceiling, to the operating table 126, which also supports the patient's body 122, or to other operating room equipment. Further, while the patient-side portion 100 is shown as including four surgical instrument manipulators 112, more or fewer surgical instrument manipulators 112 may be used. Still further, the patient-side portion 100 may consist of a single assembly as shown, or it may include two or more separate assemblies, each optionally mounted in various possible ways.

Each surgical instrument manipulator 112 supports one or more surgical instruments 120 that operate at a surgical site within the patient's body 122. Each surgical instrument manipulator 112 may be provided in a variety of forms that allow the associated surgical instrument to move with one or more mechanical degrees of freedom (e.g., all six Cartesian degrees of freedom, five or fewer Cartesian degrees of freedom, etc.). Typically, mechanical or control constraints restrict each surgical instrument manipulator 112 to move its associated surgical instrument around a center of motion on the surgical instrument that stays stationary with reference to the patient, and this center of motion is typically located to be at the position where the surgical instrument enters the body.

A functional teleoperated surgical system will generally include a vision system portion (not shown) that enables the operator to view the surgical site from outside the patient's body 122. The vision system typically includes a surgical instrument that has a video-image-capture function 128 (a "camera instrument") and one or more video displays for displaying the captured images. In some surgical system configurations, the camera instrument 128 includes optics that transfer the images from the distal end of the camera instrument 128 to one or more imaging sensors (e.g., CCD or CMOS sensors) outside of the patient's body 122. Alternatively, the imaging sensor(s) may be positioned at the distal end of the camera instrument 128, and the signals produced by the sensor(s) may be transmitted along a lead or wirelessly for processing and display on the video display. An illustrative video display is the stereoscopic display on the surgeon's console in surgical systems commercialized by Intuitive Surgical, Inc., Sunnyvale, Calif.

A functional teleoperated surgical system will further include a control system portion (not shown) for controlling the movement of the surgical instruments 120 while the instruments are inside the patient. The control system portion may be at a single location in the surgical system, or it may be distributed at two or more locations in the system (e.g., control system portion components may be in the system's patient-side portion 100, in a dedicated system control console, or in a separate equipment rack). The teleoperated master/slave control may be done in a variety of ways, depending on the degree of control desired, the size of the surgical assembly being controlled, and other factors. In some embodiments, the control system portion includes one or more manually-operated input devices, such as a joystick, exoskeletal glove, a powered and gravity-compensated manipulator, or the like. These input devices control teleoperated motors which, in turn, control the movement of the surgical instrument.

The forces generated by the teleoperated motors are transferred via drivetrain mechanisms, which transmit the forces from the teleoperated motors to the surgical instrument 120. In some telesurgical embodiments, the input devices that control the manipulator(s) may be provided at a location remote from the patient, either inside or outside the room in which the patient is placed. The input signals from the input devices are then transmitted to the control system portion. Persons familiar with telemanipulative, teleoperative, and telepresence surgery will know of such systems and their components, such as the da Vinci® Surgical System commercialized by Intuitive Surgical, Inc. and the Zeus® Surgical System originally manufactured by Computer Motion, Inc., and various illustrative components of such systems.

As shown, both the surgical instrument 120 and an optional entry guide 124 (e.g., a cannula in the patient's abdomen) are removably coupled to the distal end of a manipulator 112, with the surgical instrument 120 inserted through the entry guide 124. Teleoperated actuators in the manipulator 112 move the surgical instrument 120 as a whole. The manipulator 112 further includes an instrument carriage 130. The surgical instrument 120 is detachably connected to the carriage 130. The teleoperated actuators housed in the carriage 130 provide a number of controller motions which the surgical instrument 120 translates into a variety of movements of the end effector on the surgical instrument. Thus the teleoperated actuators in the carriage 130 move only one or more components of the surgical instrument 120 rather than the instrument as a whole. Inputs to control either the instrument as a whole or the instrument's components are such that the input provided by a surgeon to the control system portion (a "master" command) is translated into a corresponding action by the surgical instrument (a "slave" response).

Figure 2:
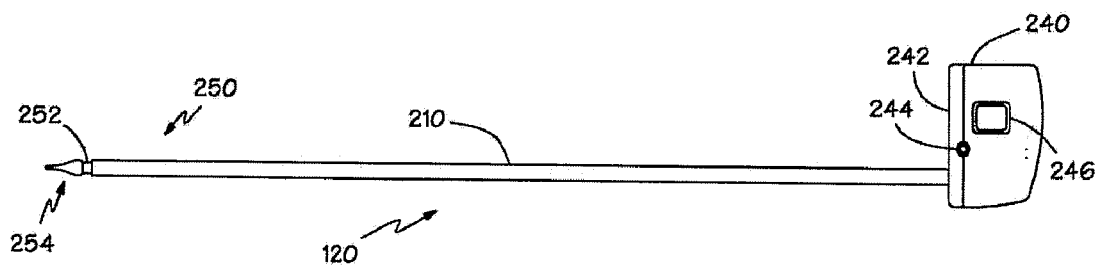
FIG. 2 is a side view of a surgical instrument for use with a teleoperated actuator.

FIG. 2 is a side view of an illustrative embodiment of the surgical instrument 120, comprising a distal portion 250 and a proximal control mechanism 240 coupled by an elongate tube 210. The distal portion 250 of the surgical instrument 120 may provide any of a variety of surgical tools, such as the forceps 254 shown, a needle driver, a cautery device, a cutting tool, an imaging device (e.g., an endoscope or ultrasound probe), or a combined device that includes a combination of two or more various tools and imaging devices. In the embodiment shown, the surgical tool 254 is coupled to the elongate tube 210 by a "wrist" 252 that allows the orientation of the surgical tool to be manipulated with reference to the instrument tube 210.

Surgical instruments that are used with the invention may control their end effectors (surgical tools) with a plurality of rods and/or flexible cables. Rods, which may be in the form of tubes, may be combined with cables to provide a "push/pull" control of the end effector with the cables providing flexible sections as required. A typical elongate tube 210 for a surgical instrument 120 is small, perhaps five to eight millimeters in diameter, roughly the diameter of a large soda straw. The diminutive scale of the mechanisms in the surgical instrument 120 creates unique mechanical conditions and issues with the construction of these mechanisms that are unlike those found in similar mechanisms constructed at a larger scale, because forces and strengths of materials do not scale at the same rate as the size of the mechanisms. The cables must fit within the elongate tube 210 and be able to bend as they pass through the wrist joint 252.

In order to provide a sterile operation area while using a functional teleoperated surgical system, it is preferred that a barrier be placed between the non-sterile system and the sterile surgical field. Therefore, a sterile component, such as an instrument sterile adapter (ISA), is placed between the surgical instrument 120 and the teleoperated surgical instrument manipulator 130. The placement of an instrument sterile adapter between the surgical instrument 120 and the surgical instrument manipulator 130 includes the benefit of ensuring a sterile coupling point for the surgical instrument 120 and the surgical instrument manipulator 130. This permits removal of surgical instruments from the surgical instrument manipulator 130 and exchange with other surgical instruments during the course of a surgery.

Figure 3A:
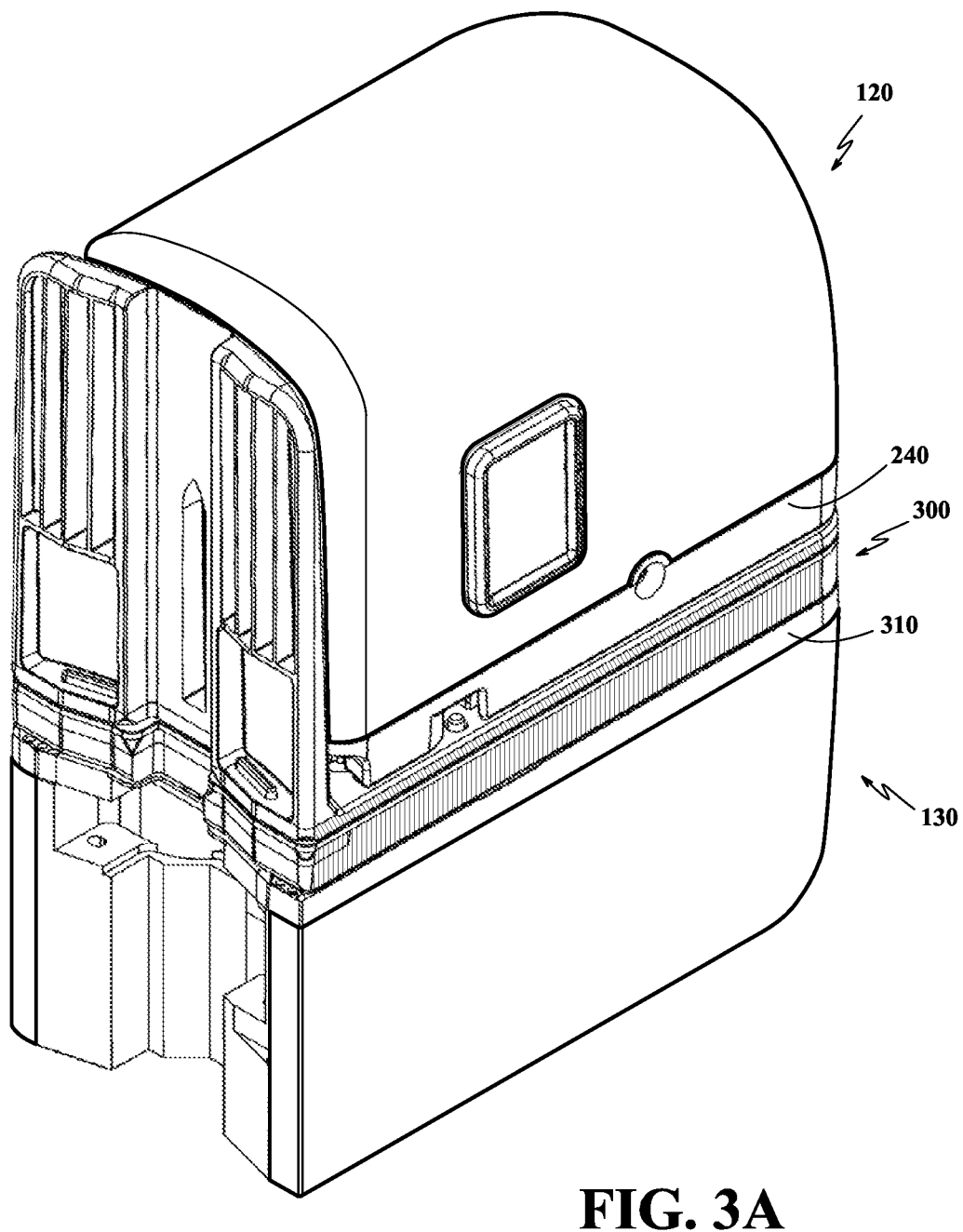
FIG. 3A is an illustration of an exemplary embodiment of a coupling of a surgical instrument, a carriage of a surgical instrument manipulator, and an instrument sterile adapter (ISA).

FIG. 3A shows a portion of an exemplary embodiment of a proximal control mechanism 240 of a surgical instrument 120, a carriage 310 of a teleoperated surgical instrument manipulator 130, and an instrument sterile adapter (ISA) 300 in a coupled condition.

Figure 3B:
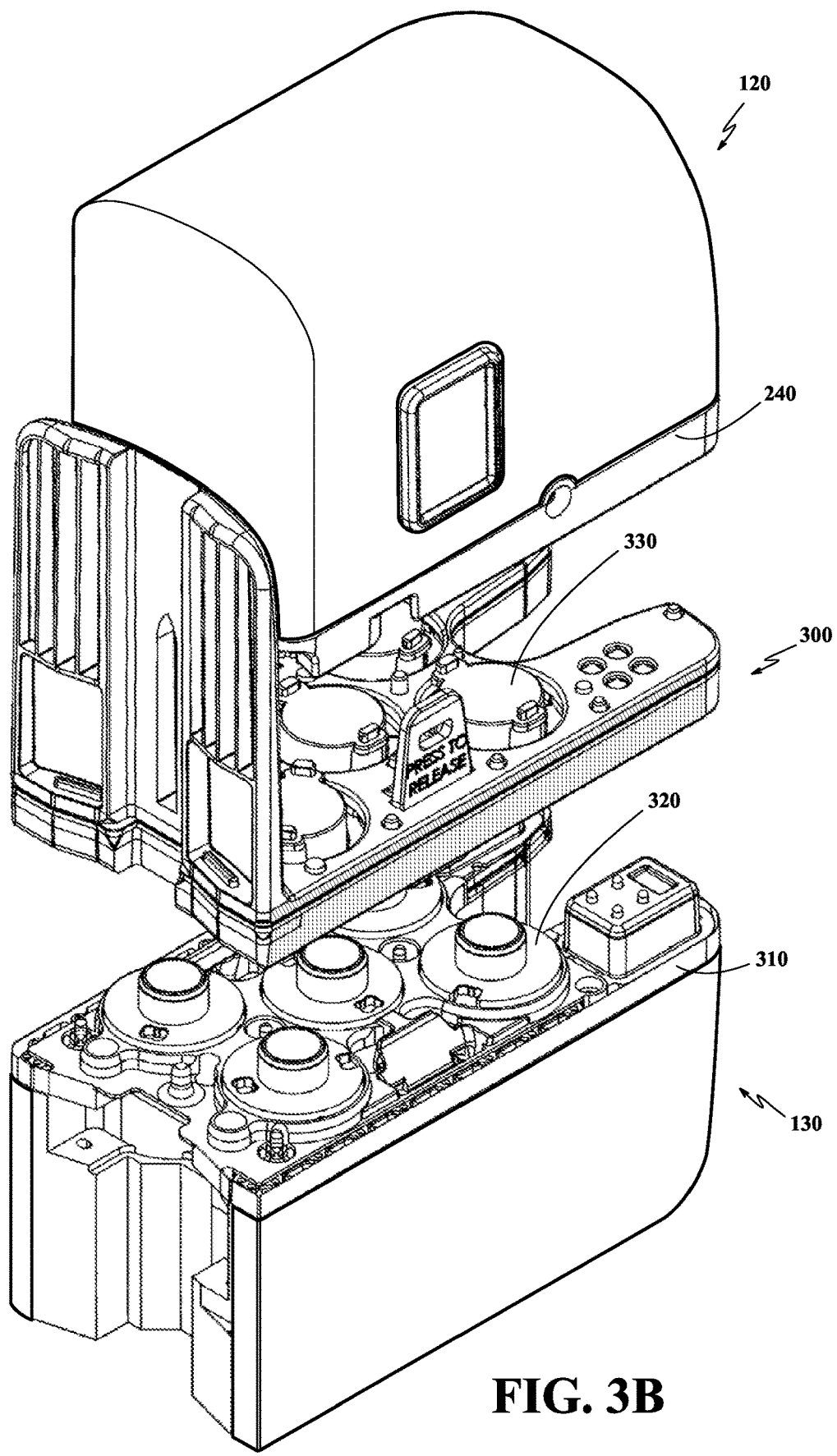
FIG. 3B is an illustration of an exemplary embodiment of the coupler system of FIG. 3A.

FIG. 3B shows an exploded view of the coupler system of FIG. 3A. In one embodiment, the first stage of the coupling process includes the ISA 300 coupling with the carriage 130. Carriage drivers 320 on the carriage 130 are rotated to engage the corresponding ISA couplers 330. The surgical instrument 120 is coupled with the ISA 300. The ISA couplers 330 are rotated by the carriage drivers 320 to engage corresponding instrument drivers (not shown).

Instrument Sterile Adapter Disk Assembly

The instrument sterile adapter (ISA) is assembled from a plurality of components, including, among others, a top component, a bottom component and one or more couplers. A coupler is positioned through an opening in the bottom component, and then the top component is joined with the bottom component.

There is a need for a mechanism that allows the top component to couple with the bottom component and ensure that couplers will not become dislodged while still allowing the couplers to rotate freely.

FIG. 4 shows an exemplary embodiment of an assembled ISA 300. The ISA 300 includes an ISA top component 410, an ISA bottom component 420, and a plurality of ISA couplers 330. The embodiment of FIG. 4 illustrates the ISA 300 including five ISA couplers 330. The number of ISA couplers 330 is not limited to five, but may be more than or less than five.

Referring to FIG. 5, a view of an ISA bottom component 420 and a plurality of ISA couplers 330 is shown. The ISA bottom component 420 includes a plurality of bottom component openings 530. Each coupler 330 is associated with a corresponding opening 530. Each bottom component opening 530 is partially surrounded by a bottom lip 540, and each bottom lip 540 includes one or more keyways 550.

Figure 6:
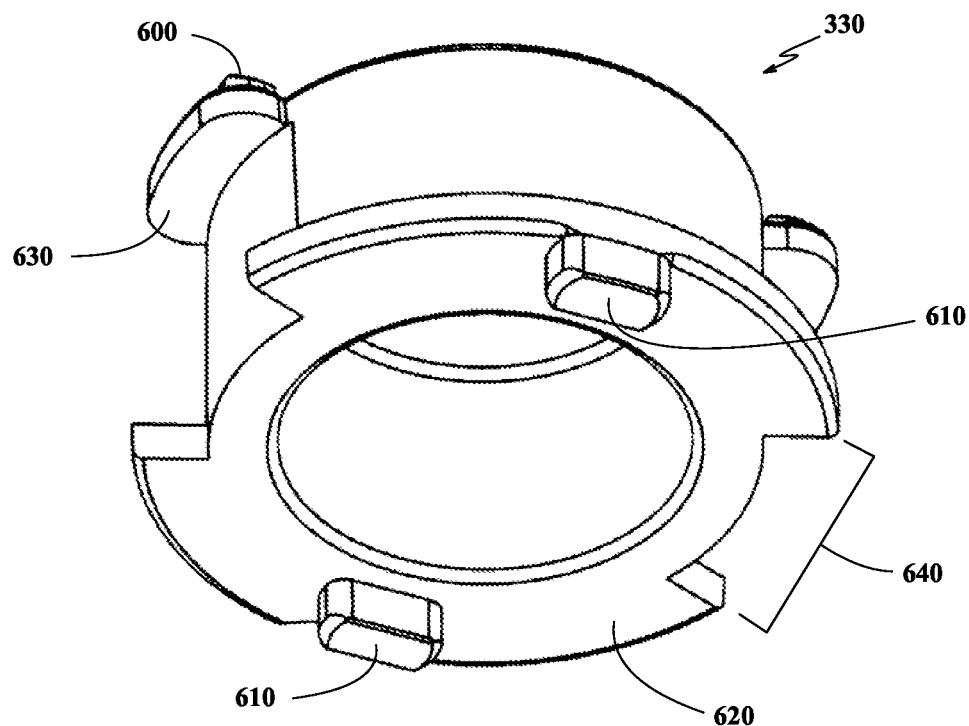
FIG. 6 is an illustration of an exemplary embodiment of an ISA coupler.

Referring to FIG. 6, an exemplary embodiment of an ISA coupler 330 is shown. The ISA coupler 330 includes two ISA bottom engagement features 610, two ISA top engagement features 600 (one is hidden from view), two ISA locking mechanism openings 640, two retention tabs 630, and an ISA coupler lip 620. It should be noted that the number of engagement features, retention tabs, and locking mechanism openings are variable. In addition, various configurations of the top and bottom engagement features 600, 610 may be used. For example, the bottom engagement feature 610 could be a recessed feature rather than a projecting feature as shown.

Referring again to FIG. 5, each ISA coupler 330 is positioned in a corresponding bottom component opening 530. The ISA coupler 330 is rotated to align the retention tabs 630 with the keyways 550 to allow the ISA coupler to be inserted into the corresponding bottom component opening 530. The ISA coupler lip 620 is larger than the bottom component opening 530 and limits the distance the ISA coupler 330 can be inserted into the bottom component opening. The ISA coupler 330 is then rotated to unalign the retention tabs 630 with the keyways 550 so as to retain the ISA coupler in the corresponding bottom component opening 530.

Figure 7:
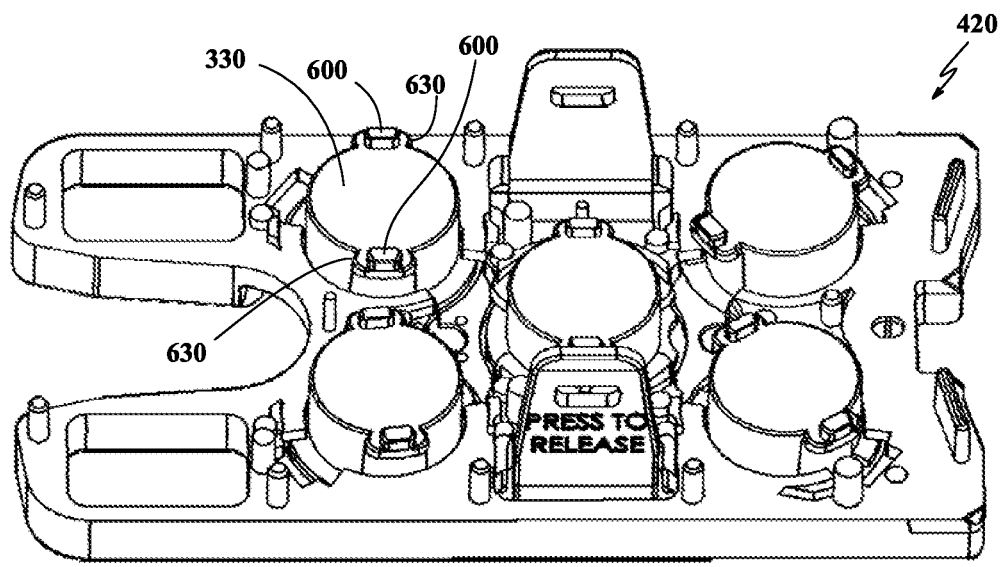
FIG. 7 is an illustration of a plurality of ISA couplers coupled with the ISA bottom component.

Referring to FIG. 7, an illustration of a plurality of ISA couplers 330 coupled with the ISA bottom component 420 is shown.

Figure 8:
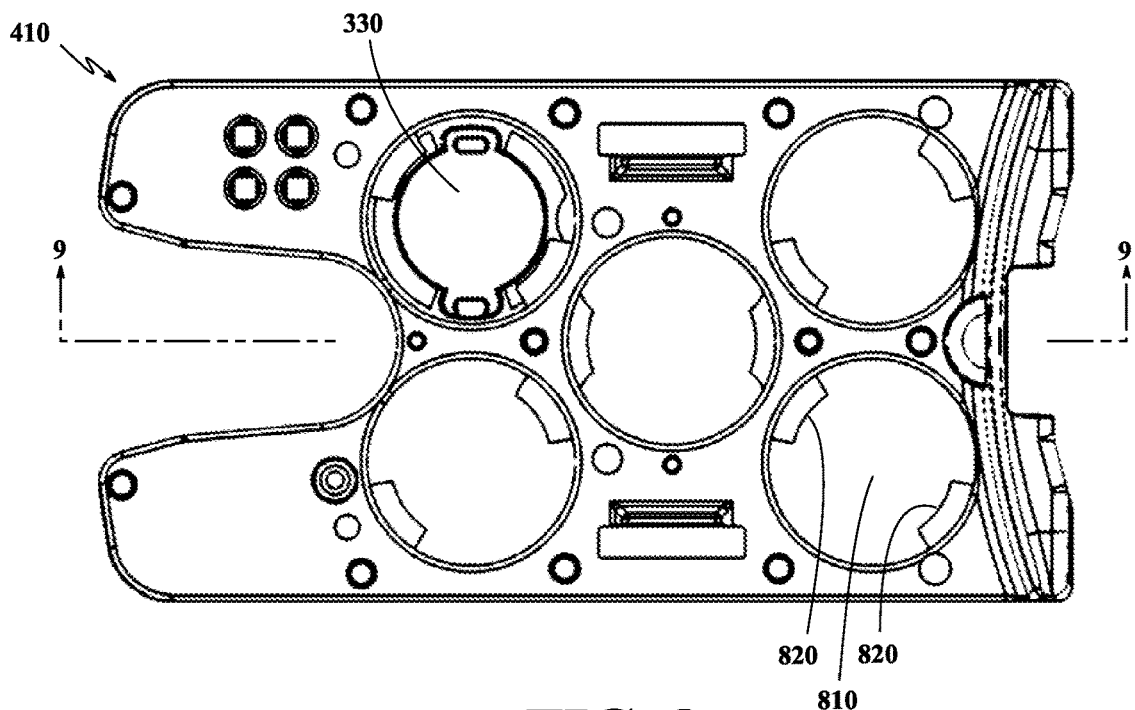
FIG. 8 is an illustration of an exemplary embodiment of an ISA top component having one ISA coupler placed in a top component opening.

Referring to FIG. 8, one exemplary embodiment of the ISA top component 410 is illustrated. In FIG. 8, the ISA top component 410 of the ISA 300 includes five top component openings 810, through which five ISA couplers 330 pass. Furthermore, each top component opening 810 includes two keyway fillers 820. The number of keyway fillers 820 included in each top component opening 810 may be varied but should correspond with the number of keyways 550 included in each bottom component opening 530 of the ISA bottom component 420.

Figure 9:
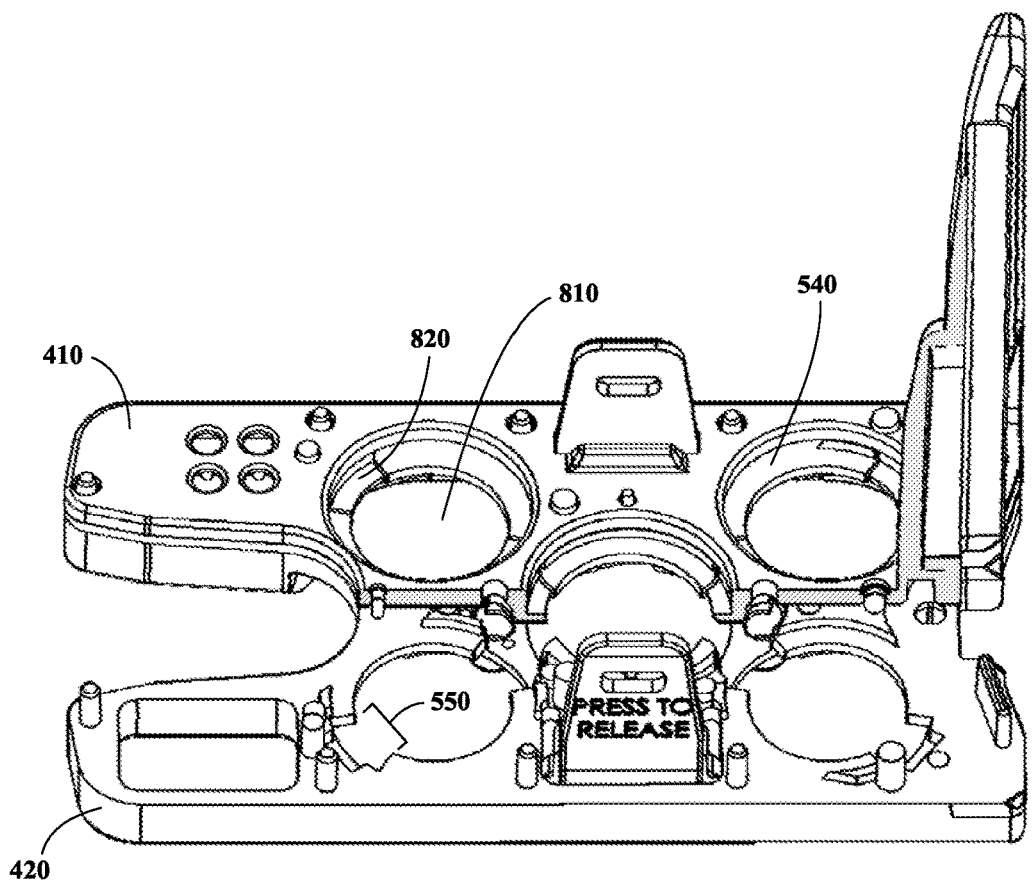
FIG. 9 is illustration of a cut-away ISA top component coupled to the ISA bottom component without the ISA couplers.

FIG. 9 illustrates the ISA top component 410 coupled to the ISA bottom component 420. The ISA couplers 330 are not shown to allow the bottom lip 540 and keyway 550 features of the bottom component to be seen. Furthermore, FIG. 9 illustrates the ISA top component 410 cut along line 9-9 in FIG. 8 and the forward half of the ISA top component removed. After the ISA couplers 330 are inserted into the corresponding bottom component openings 530, the ISA top component 410 is then placed on top of the ISA bottom component 420 such that the ISA couplers 330 pass through the corresponding top component openings 810 in the ISA top component 410.

The keyway fillers 820 of the ISA top component 410 align with the keyways 550 of the ISA bottom component 420. When the ISA top component 410 is assembled with the ISA bottom component 420, the alignment of the keyway fillers 820 and the keyways 550 locks the ISA couplers 330 between the ISA bottom component 420 and the ISA top component 410. The illustration of FIG. 9 shows that the keyway filler 820 of the top component 410 and the bottom lip 540 of the bottom component 420 create a complete lip when the top component 410 and then bottom component 420 are coupled.

Figure 10:
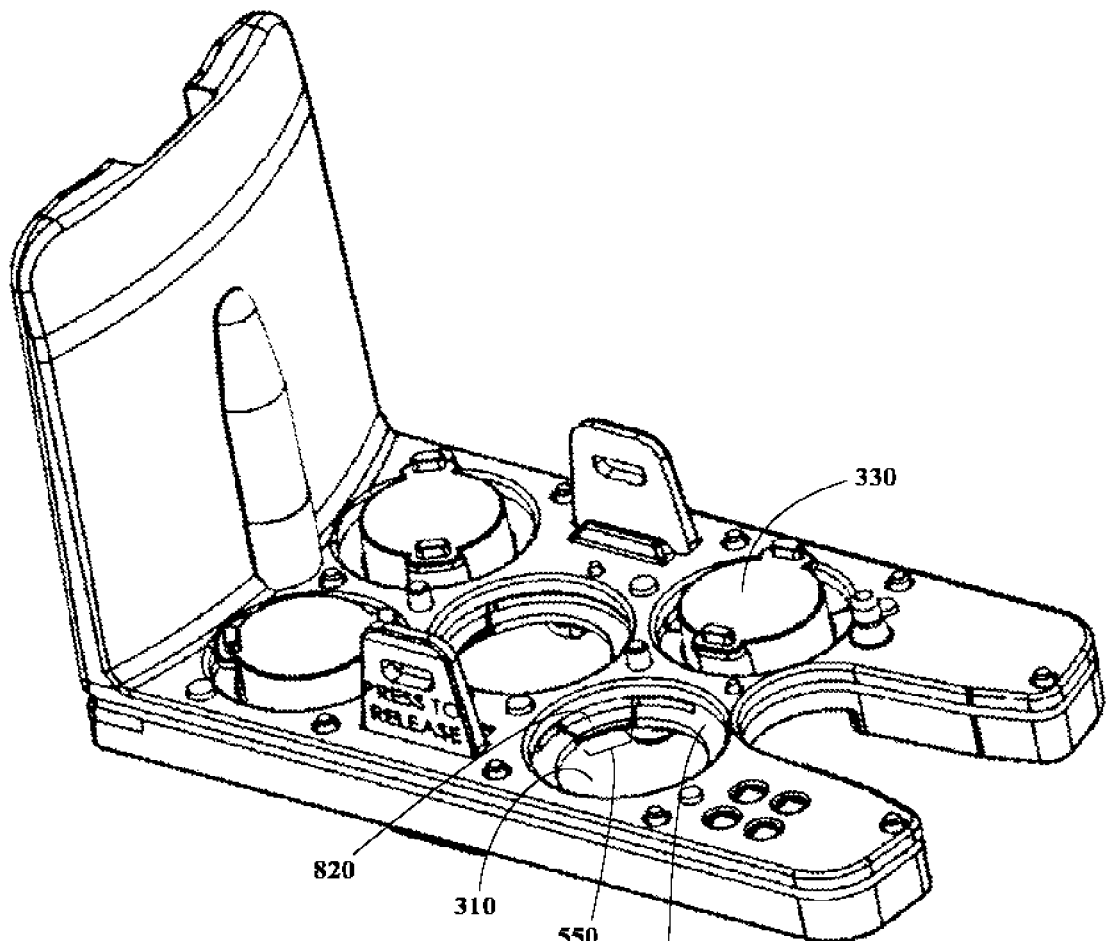
FIG. 10 is an illustration of an exemplary embodiment of a top component of the ISA coupled to a bottom component of the ISA without an ISA coupler.

FIG. 10 illustrates an exemplary embodiment of the ISA top component 410 coupled to the bottom component 700 without the ISA coupler 330 in two of the openings 870. The ISA coupler 330 is not shown in FIG. 10 in order to illustrate how the keyway filler 820 aligns with the keyway 550 to create a solid lip preventing the ISA coupler 330 from dislodging. As is seen in FIG. 10, the keyway filler 820 is configured to be the counterpart to the keyway 550. Of course, other shapes may be used for the keyways 550 and the keyway fillers 820.

Instrument Sterile Adapter Engagement

Figure 11:
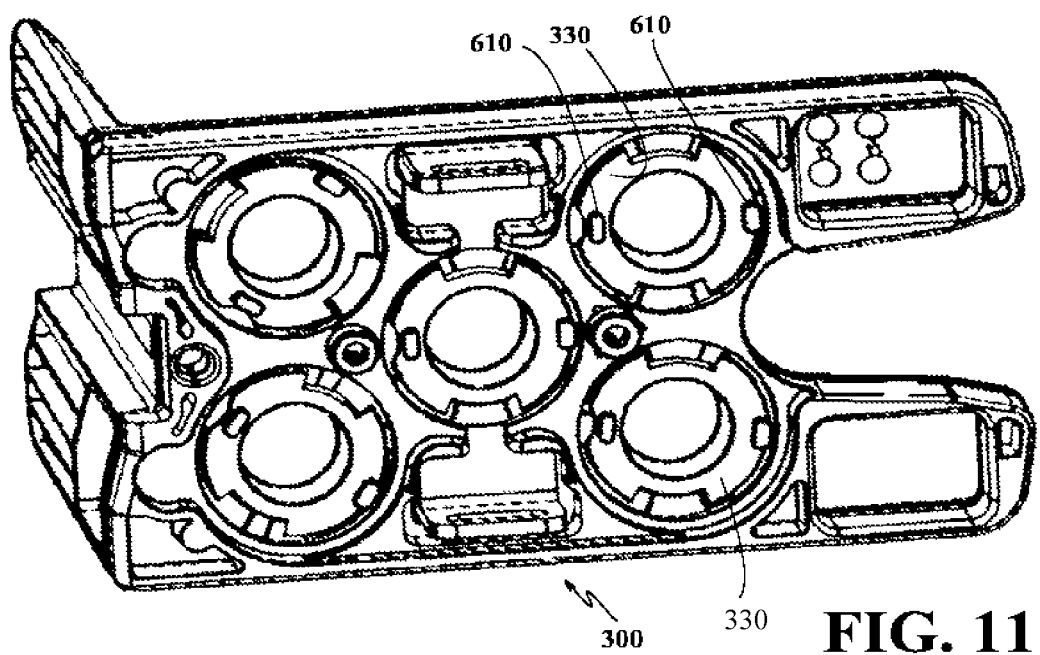
FIG. 11 is an illustration of an exemplary embodiment of the underside of an ISA.

Referring to FIG. 11, an exemplary illustration of the underside of the ISA 300 is shown. In the embodiment, the ISA 300 is shown to include five ISA couplers 330. However, the number of ISA couplers 330 is not limited to five; other embodiments may contain more than or less than five. Furthermore, the placement of the ISA couplers 330 is not limited to that as illustrated in FIG. 11, and ISA couplers may be arranged in various patterns.

As discussed above, FIG. 6 shows an exemplary embodiment of an ISA coupler 330. In the embodiment shown, the ISA coupler 330 includes two ISA bottom engagement features 610, two ISA top engagement features 600, two ISA locking mechanism openings 640, two retention tabs 630, and an ISA coupler lip 620. The portion of the ISA coupler 330 that includes the ISA bottom engagement features 610 projects through the bottom component opening 530. The portion of the ISA coupler 330 that includes the ISA top engagement features 600 projects through the top component opening 810. It should be noted that there may be a different number of engagement features, retention tabs, and locking mechanism openings than the number of any or all such features shown in the drawings. Any or all of the features shown in the exemplary embodiment of FIG. 6 may be placed in different positions than those shown.

Figure 12:
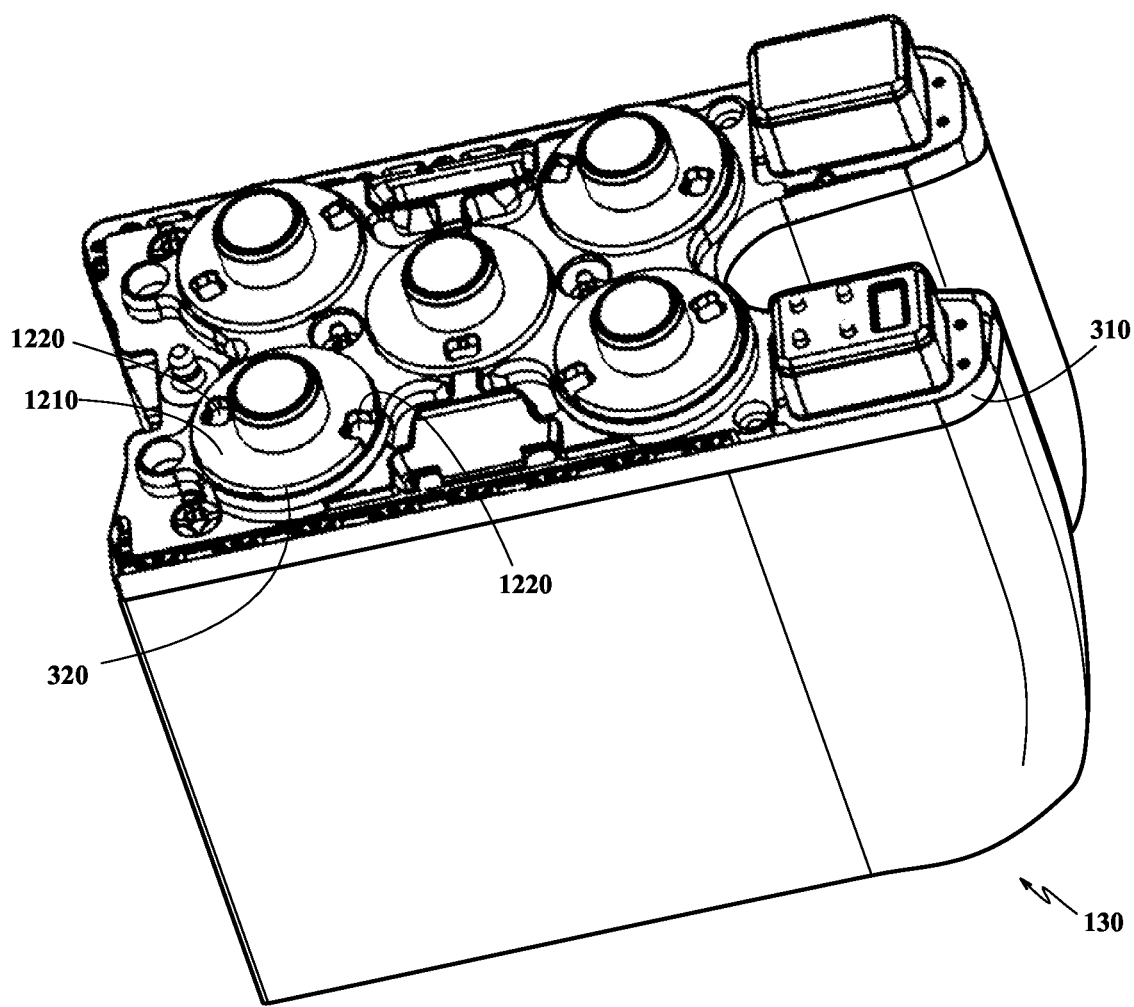
FIG. 12 is an illustration of an exemplary embodiment of an instrument carriage.

Referring to FIG. 12, an exemplary illustration of the carriage 310 is shown. In the exemplary embodiment of FIG. 12, the carriage 310 is shown to have five carriage drivers 320. Each carriage driver 320 is driven in a rotational manner by a motor (not shown). The number of carriage drivers 320 and motors can be varied depending on various factors such as, among other things, the size of the support assembly 110 and the size of the teleoperated surgical instrument manipulator 130.

In the embodiment illustrated in FIG. 12, each carriage driver 320 is shown to have two carriage engagement features 1220. The carriage 310 of the surgical instrument manipulator 130 couples with the ISA 300 through an engagement process between the carriage engagement features 1220 of the carriage driver 320 and the ISA bottom engagement features 610 of the ISA coupler 330, which will be described below. Of course, the number of carriage engagement features 1220 and ISA bottom engagement features 610 is not limited to two. In other embodiments, the number may be more than or less than two.

Each carriage driver 320 contains a spring-loaded mechanism such that when a force is applied to the carriage driver 320 (e.g., from projecting engagement features on a corresponding driven element), the carriage driver 320 recedes slightly into the carriage 310. When the carriage engagement features 1220 and ISA bottom engagement features 610 are in misalignment at the time the ISA 300 and the surgical instrument manipulator 130 attempt to engage, the spring-loaded mechanism provides the necessary force to couple the ISA bottom engagement features 610 with the carriage engagement features 1220 when they come into alignment as the carriage drivers 320 rotate.

However, the addition of an ISA 300 between the coupling of the surgical instrument 120 and the surgical instrument manipulator 130 creates a need for a way to ensure that the instrument sterile adapter properly engages with both the surgical instrument 120 and the surgical instrument manipulator 130.

If the ISA bottom engagement features 610 (FIG. 11) and the carriage engagement features 1220 are not initially in alignment when an attempt to couple the ISA 300 and the carriage 310 is made, the ISA bottom engagement features 610 will come into contact with the carriage drivers 320. To correct the misalignment, the carriage drivers 320 rotate in order to align the ISA bottom engagement features 610 and the carriage engagement features 1220. However, due to friction that is created when the ISA bottom engagement features 610 come into contact with the carriage driver disk 320, the ISA couplers 330 may rotate as the carriage drivers 320 turn. It is necessary to ensure that the ISA bottom engagement features 610 engage the carriage engagement features 1220 so that a surgical instrument attached to the ISA 300 can be properly controlled.

In order to ensure that the friction caused by the ISA bottom engagement features 610 coming in contact with the carriage disks 320 does not prevent a proper engagement between the ISA bottom engagement features 610 and the carriage engagement features 1220, a locking mechanism may be implemented within the ISA 300.

The locking mechanism implemented within the ISA 300 is a mechanism that restricts the ability of each ISA coupler 330 to rotate, at least during the engagement process with the carriage 310 of the surgical instrument manipulator 130. Therefore, if the ISA bottom engagement features 610 and the carriage engagement features 1220 are not aligned when an attempt to couple the ISA 300 with the surgical instrument manipulator 130 is made, and if the locking mechanism restricts the ability of the ISA couplers 330 to rotate, the carriage drivers 320 will be able to rotate and align the carriage engagement features 1220 with the ISA bottom engagement features 610. When the carriage engagement features 1220 come into alignment with the ISA bottom engagement features 610, the pressure created by the spring-loaded mechanism of the carriage drivers 320 causes the ISA bottom engagement features 610 to be inserted into the corresponding carriage engagement features 1220, therefore producing a proper engagement event.

FIG. 13A illustrates an embodiment of an ISA bottom component 420. As discussed above, the ISA bottom component 420 includes a plurality of bottom component openings 530. Furthermore, each bottom component opening 530 is partially surrounded by a bottom lip 540, and each bottom lip 540 includes one or more keyways 550 and one or more locking mechanisms 1310.

Prior to any coupling with the carriage 310 or the surgical instrument 120, the ISA coupler 330 does not sit flush against the bottom lip 540 or the locking mechanism(s) 1310 and is free to rotate completely in either direction. However, when an attempt to couple the carriage 310 with the ISA 300 is made, the carriage drivers 320 push the ISA couplers 330 against the bottom lip 540 or the locking mechanism(s) 1310. When the ISA coupler 330 is pushed up toward the bottom lip 540, one of two situations occur: (1) the ISA coupler lip 620 comes in contact with the locking mechanism(s) 1310 or (2) the ISA locking mechanism opening 640 and the locking mechanism 1310 are in alignment and the ISA coupler lip 620 is pushed flush against the bottom lip 540.

As seen in the detail shown in FIG. 13B, the locking mechanism 1310 is illustrated as a boss. When the ISA locking mechanism opening 640 is aligned with the ISA locking mechanism 1310, the ISA coupler 330 is pushed flush against the bottom lip 540. However, when the ISA locking mechanism opening 640 and the locking mechanism 1310 are not aligned, the ISA coupler rotates with the carriage drivers 310 against the bottom lip 540 until the ISA locking mechanism opening(s) 640 and the locking mechanism(s) 1310 are aligned. When the locking mechanism opening(s) 610 and the locking mechanism(s) 1310 are aligned, the ISA coupler lip 620 is pushed flush against the bottom lip 540. When the ISA coupler lip 620 is pushed flush against the bottom lip 540 and the locking mechanism 1310 is embodied as a boss, the ISA coupler 330 is prevented from rotating in either direction.

However, if the ISA bottom engagement features 610 and the carriage engagement features 1220 are not initially aligned at the time the carriage drivers 320 come in contact with the ISA couplers 330, the friction between the ISA couplers 330 and carriage drivers 320 will cause the ISA couplers 330 to rotate with the carriage drivers 320. Once the ISA couplers 330 rotate such that the ISA locking mechanism opening(s) 640 are aligned with the locking mechanism(s) 1310, the ISA coupler lip 620 will be pushed flush against the bottom lip 540. The torque from the motors is more powerful than the friction created by the force of the spring-loaded mechanisms in the carriage drivers 320 so the carriage drivers 320 continue to rotate as the ISA couplers remain stationary. As the carriage drivers 320 rotate, it will bring the carriage engagement features 1220 into alignment with the ISA bottom engagement features 610. When the carriage engagement features 1220 and the ISA bottom engagement features 610 are in alignment, the pressure from the spring-loaded mechanism of the carriage 310 will cause the carriage engagement features 1220 and the ISA bottom engagement features 610 to engage.

In the embodiment shown in FIG. 13C, the locking mechanism 1320 is illustrated as a ratchet. FIG. 13D is a detail drawing of a portion of FIG. 13C that shows the ratchet locking mechanism. When the ISA locking mechanism opening(s) 640 and the locking mechanism(s) 1320 are not aligned, due to the friction created by the spring-loaded mechanism of the carriage drivers 320, the ISA couplers 330 rotate with the carriage drivers 310 until the ISA locking mechanism opening(s) 640 and the locking mechanism(s) 1320 are aligned. When the locking mechanism 1320 is embodied as a ratchet, the ISA coupler lip 620 slides along in the slip direction of the ratchet until it hits a ratchet wall. When the ISA coupler 330 has slid along the slip and hit the ratchet wall, the ISA coupler lip 620 sits flush against the bottom lip 540. When the ISA coupler lip 620 is pushed flush against the bottom lip 540 and the locking mechanism 1320 is embodied as a ratchet, the ISA coupler 330 is prevented from rotating in the direction against the ratchet wall.

When the locking mechanism 1320 is embodied as a ratchet, the motors that drive the carriage drivers 320 are configured to rotate the carriage drivers 320, and consequently the ISA couplers 330, in the direction against the ratchet. If the ISA bottom engagement features 610 and the carriage engagement features 1220 are not initially aligned at the time the carriage drivers 320 come in contact with the ISA couplers 330, the friction between the ISA couplers 330 and carriage drivers 320 will cause the ISA couplers 330 to rotate with the carriage drivers 320. The torque from the motors is more powerful than the friction created by the force of the spring-loaded mechanisms in the carriage drivers 320 so once the ISA coupler lip 620 rotates to hit the ratchet wall, the carriage drivers 320 continue to rotate as the ISA couplers remain stationary. As the carriage drivers 320 rotate, it will bring the carriage engagement features 1220 into alignment with the ISA bottom engagement features 610. When the carriage engagement features 1220 and the ISA bottom engagement features 610 are in alignment, the pressure from the spring-loaded mechanism of the carriage 310 will cause the carriage engagement features 1220 and the ISA bottom engagement features 610 to engage.

When the locking mechanism 1320 is embodied as a ratchet, once the ISA coupler 330 is properly engaged with the carriage drivers 320, it is possible to rotate the ISA coupler 330 in the direction opposite that in which the ISA coupler lip 620 rotates to hit the ratchet wall. This allows the ISA coupler 330 to be rotated to a desired position prior to engaging a surgical instrument manipulator 130 with the ISA 300.

Thereafter, in both embodiments illustrated in FIGS. 13A-B, once the ISA coupler 330 is properly engaged with the carriage drivers 320, it is preferable for the ISA coupler 330 to be permitted to rotate freely in either direction. As the instrument drivers 710 of the instrument 120 attempt to couple with the ISA couplers 330, the instrument drivers 710 place pressure on the ISA couplers 330. This in turn presses the ISA coupler lip 620 below the depth of the locking mechanism 1310 or 1320, and allows the ISA coupler 330 to avoid the locking mechanism 1310 or 1320 and rotate freely in either direction.

Furthermore, it is not necessary for the pockets to be located on the carriage drivers 320 and the bosses to be located on the ISA couplers 330 as shown in the figures provided. Instead, one embodiment may have the carriage drivers 320 including bosses and the ISA couplers 330 including pockets. In another embodiment, the locking mechanism may be formed on the ISA top component 410 and extend into the ISA bottom component 420.

In one embodiment, the teleoperated surgical instrument manipulator 130 includes a software module that enables the surgical instrument manipulator 130 to detect when a proper engagement between the ISA 300 and the surgical instrument manipulator 130 (through the ISA couplers 330 and the carriage drivers 310) has occurred. A proper engagement event may be detected by the software module through the analysis of the amount of torque applied to the motors of the carriage 310. When a proper engagement has occurred, the ISA bottom engagement features 610 have coupled with the carriage engagement features 1220 and the motors are attempting to drive the ISA couplers 330 against restriction of the locking mechanism. In this case, the software module detects an increased torque on each motor. The detection of this increased torque indicates a proper engagement and the absence of the increased torque indicates that the ISA bottom engagement features 610 have not successfully coupled with the carriage engagement features 1220.

The software module may communicate the absence or completion of a proper engagement to surgical personnel. This communication may occur in numerous ways. Examples of possible ways a proper engagement may be communicated are, among other things, flashing a light on the surgical instrument manipulator 130 or changing a light of a first color on the surgical instrument manipulator 112 to a second color (such as red to green).

High Speed Disk Engagement

As discussed above, the addition of an instrument sterile adapter (ISA) between the coupling of the surgical instrument 120 and the surgical instrument manipulator 130 creates a need for a way to ensure that the ISA properly engages with both the surgical instrument 120 and the surgical instrument manipulator 130.

Figure 14:
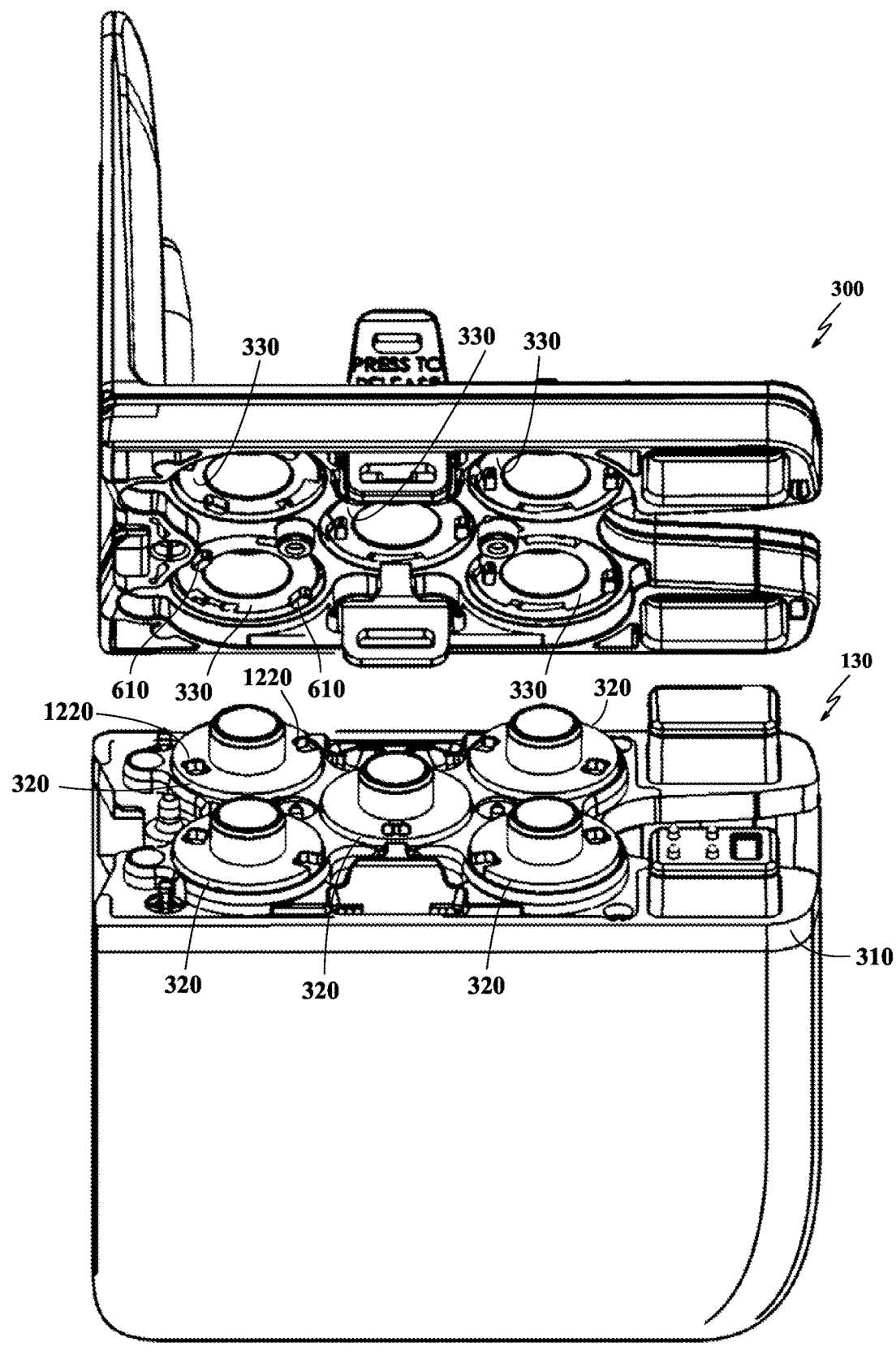
FIG. 14 is an illustration of an exemplary embodiment of an ISA and a surgical manipulator.

FIG. 14 shows an embodiment of the ISA 300 and the surgical instrument manipulator 130 with the ISA and the surgical instrument manipulator rotated away from each other to show the surfaces that engage each other. As previously discussed, the surgical instrument manipulator 130 includes one or more carriage drivers 320 that provide rotary motion to drive a surgical instrument. The ISA includes a like number of ISA couplers 330 that transfer the rotary motion from the carriage drivers 320 to the surgical instrument. In the embodiment shown, each carriage driver 320 includes two carriage engagement features 1220 in form of pockets. The corresponding ISA coupler 330 includes a like number of ISA bottom engagement features 610 in the form of bosses. Each ISA engagement feature 610 mates with a corresponding carriage engagement feature 1220 to provide a positive connection between the carriage driver 320 and the ISA coupler 330. In other embodiments different numbers of engagement features may be used. In other embodiments the carriage engagement features may be in form of bosses and the ISA bottom engagement features may be in the form of pockets. In still other embodiments the carriage engagement features may include both pockets and bosses and the ISA bottom engagement features may be in the form of bosses and pockets as necessary to mate with the corresponding carriage engagement features.

Figure 15:
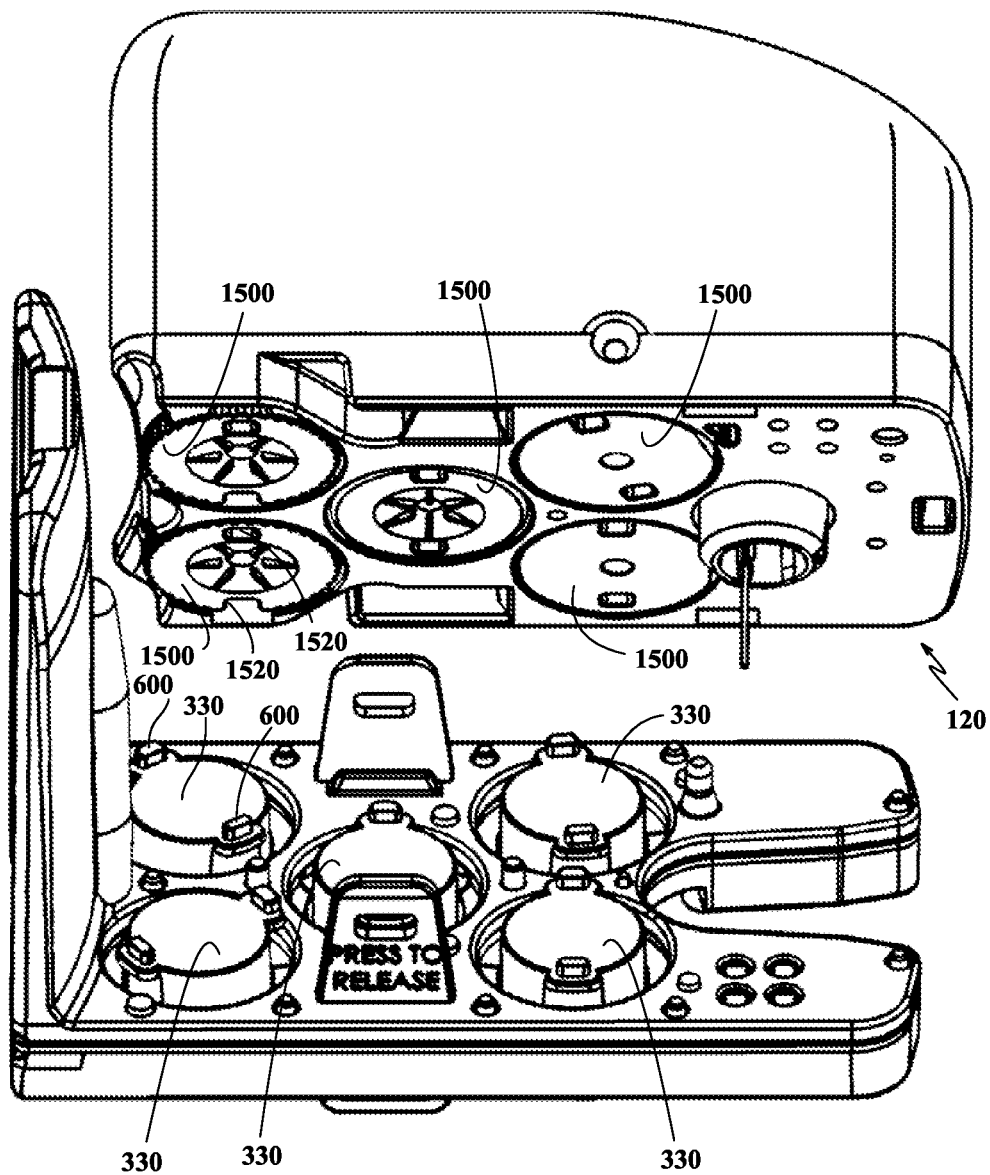
FIG. 15 is an illustration of an exemplary embodiment of an ISA and a surgical instrument.

FIG. 15 shows an embodiment of the ISA 300 and a surgical instrument 120 with the ISA and the surgical instrument rotated away from each other to show the surfaces that engage each other. As previously discussed, the ISA couplers 330 engage corresponding instrument drivers 1500 to transfer the rotary motion from the carriage drivers 320 (FIG. 14) to the surgical instrument 120. In the embodiment shown, each instrument driver 1500 includes two instrument engagement features 1520 in form of pockets. The corresponding ISA coupler 330 includes a like number of ISA top engagement features 600 in the form of bosses. Each ISA engagement feature 600 mates with a corresponding instrument engagement feature 1520 to provide a positive connection between the ISA coupler 330 and the instrument driver 1500. In other embodiments different numbers of engagement features may be used. In other embodiments the instrument engagement features may be in form of bosses and the ISA top engagement features may be in the form of pockets. In still other embodiments the instrument engagement features may include both pockets and bosses and the ISA top engagement features may be in the form of bosses and pockets as necessary to mate with the corresponding instrument engagement features.

One solution presented above discusses implementing a locking mechanism in the ISA 300 which restricts ability of the ISA couplers 330 to rotate during the engagement process, thereby ensuring that the friction caused by the ISA bottom engagement features 610 coming into contact with the carriage disks 320 did not prevent a proper engagement between the ISA bottom engagement features 610 and the carriage engagement features 1220.

However, even if the locking mechanism is implemented in the ISA 300, it may take several rotations of the carriage drivers to ensure a successful engagement of the ISA engagement features 600, 610 with the corresponding carriage and instrument engagement features 1220, 1520.

First Embodiment

In a first embodiment, the motors may be limited as to the rotational speed of the carriage drivers 320. By limiting the rotational speed of the carriage drivers 320, it can be ensured that the spring-loaded mechanism of the carriage drivers 320 will be sufficiently strong to engage the ISA bottom engagement features 610 with the carriage engagement features 1220. Likewise the limited rotational speed of the carriage drivers 320 allows the spring-loaded mechanism of the instrument drivers 1520 to reliably engage the ISA top engagement features 600. In some embodiments only the carriage drivers provide a spring-loaded mechanism that cause engagement of both the carriage engagement features with the ISA bottom engagement features and the ISA top engagement features with the instrument engagement features.

In one embodiment, a limitation of the rotational speed of the motors that drive the carriage drivers 320 may be controlled by a software module. In a second embodiment, the rotational speed of the motor may be limited by the applied voltage, current, and/or frequency of the current. The appropriate rotational speed of the carriage drivers 320 may be established by an analysis of the geometry and physics associated with the ISA couplers 330, the carriage and instrument drivers 320, 1520, and the associated spring-loaded mechanisms.

Second Embodiment

In some embodiments, the engagement feature configured as a pocket may be configured with an entry ramp to increase the ease of the process of mating with the engagement feature configured as a boss.

For ease of explanation, the engagement features to couple the carriage 310 and the ISA 300 will be described. However, it should be understood that these features may also be used to couple the instrument 120 and the ISA 300. In the embodiments discussed below, it will be assumed that the engagement feature of the carriage 310 is configured as a pocket and the engagement figure of the ISA 300 is configured as a boss. However, in another embodiment, the engagement feature of the carriage 310 may be configured as a boss and the engagement feature of the ISA 300 may be configured as a pocket.

Figure 16A:
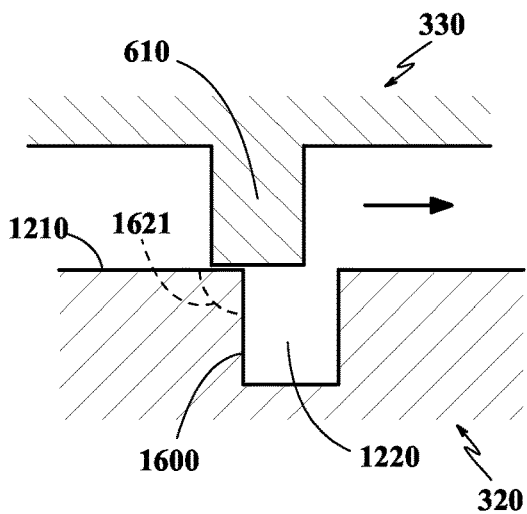
FIG. 16A is an illustration of an exemplary embodiment of an ISA bottom engagement feature approaching a carriage engagement feature without an entry ramp.

Referring to FIG. 16A, an exemplary illustration of an ISA bottom boss 610 approaching a carriage pocket 1220 without an entry ramp is illustrated. It is seen in FIG. 16A that carriage pocket wall 1600 is at a 90-degree angle 1621 in relation to the surface 1210 of the carriage disk 320. The ISA bottom boss 610 will insert into the carriage pocket 1220 only when the two engagement features are in direct alignment. The size of the protrusion of the ISA bottom boss 610 will correspond almost exactly to size of the opening of the carriage pocket 1220 to decrease the backlash that may arise during rotation of the carriage drivers 320 and the ISA couplers 330 after a successful proper engagement. Therefore, it is difficult for the ISA bottom boss 610 to be inserted into the carriage pocket 1220, especially when the carriage drivers 320 are rotating at a high speed.

Figure 16B:
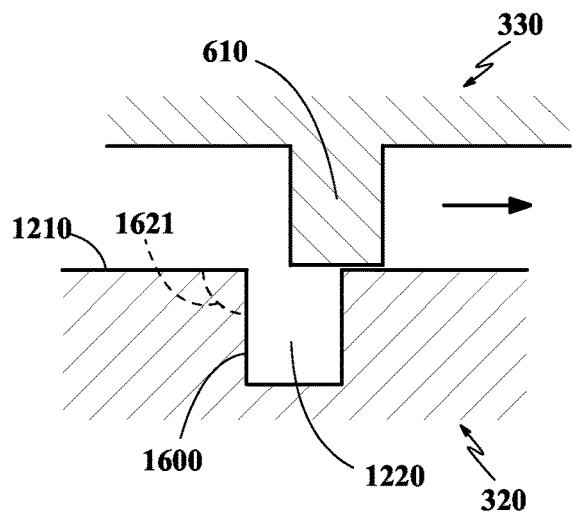
FIG. 16B is an illustration of the exemplary embodiment of FIG. 14A showing a failed attempt at coupling the ISA bottom engagement feature with the carriage engagement feature.

Referring to FIG. 16B, an exemplary illustration of a failed attempt at coupling the ISA bottom boss 610 with the carriage pocket 1220 is illustrated. As is seen in FIG. 16B, the ISA bottom boss 610 may bypass the carriage pocket 1220, resulting in a failed attempt to couple the two engagement features.

Figure 17A:
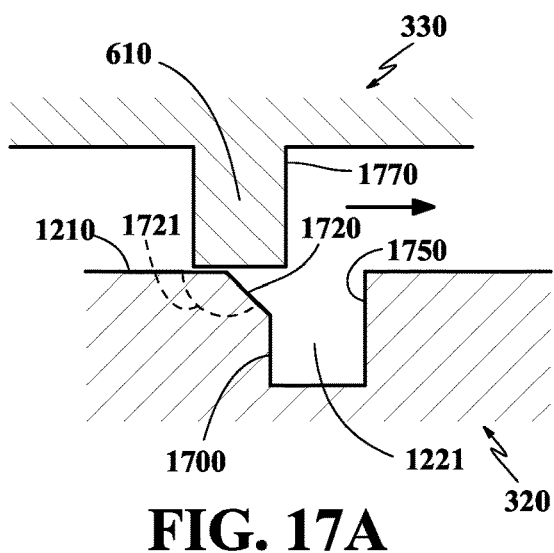
FIG. 17A is an illustration of an exemplary embodiment of an ISA bottom engagement feature approaching a carriage engagement feature that includes an entry ramp.

Referring to FIG. 17A, an exemplary illustration of an ISA bottom boss 610 approaching a carriage pocket 1221 including an entry ramp 1720 is illustrated. It is seen in FIG. 17A that a wall of the carriage pocket 1221 includes an entry ramp 1720 and a straight portion 1700. The entry ramp 1720 is seen to form an obtuse angle of more than 90 degrees in relation to the surface 1210 of the carriage disk 320 that supports the ISA bottom boss 610 before it engages the carriage pocket 1221. When the ISA bottom boss 610 approaches the carriage pocket 1221, the entry ramp 1720 allows the ISA bottom boss 610 to begin insertion into the carriage pocket 1221 before the leading ISA boss wall 1770 reaches the trailing pocket wall 1750.

Figure 17B:
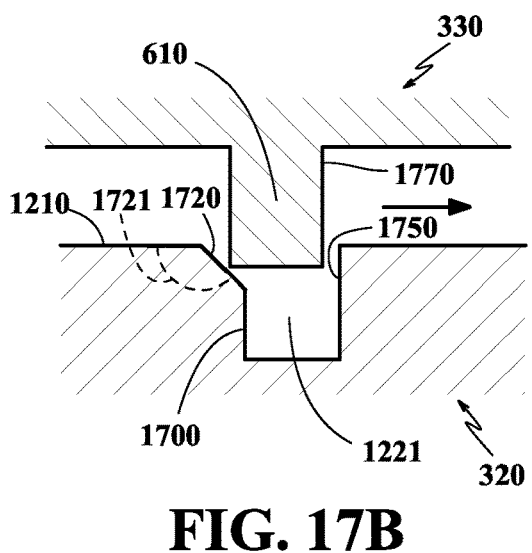
FIG. 17B is an illustration of the exemplary embodiment of FIG. 15A showing the ISA bottom engagement feature approaching the carriage engagement feature and using the entry ramp to begin mating with the carriage engagement feature.

Referring to FIG. 17B, an exemplary illustration of an ISA bottom boss 610 approaching a carriage pocket 1221 and using the entry ramp 1720 to begin insertion into the carriage pocket 1221 is shown. When the ISA bottom boss 610 begins sliding down the entry ramp 1720, the ISA boss 1760 begins to enter carriage pocket 1221. As the ISA coupler 330 continues to rotate, the leading ISA boss wall 1770 comes in contact with the trailing pocket wall 1750 and the ISA bottom boss 610 is prevented from bypassing the carriage pocket 1221. The spring-loaded mechanism of the carriage driver 320 is then able to propel the insertion of the ISA bottom boss 610 into the carriage pocket 1221. As suggested by FIG. 17B, if the carriage driver 320 contains a spring-loaded mechanism, the carriage driver 320 will rise from the carriage to cause the ISA bottom boss 610 to enter the carriage pocket 1221.

The angle 1721 of entry ramp 1720 in relation to the surface 1210 of the carriage disk 320 shown is only one exemplary embodiment. The angle of the entry ramp may be more than or less than the angle 1721 shown. However, the entry ramp 1720 will always form an obtuse angle with the surface 1210 of the carriage disk 320. It will be appreciated that the entry ramp 1720 should be configured so that the straight portion 1700 of the wall of the carriage pocket 1221 provides an adequate bearing surface to support the ISA bottom boss 610 when driven against the straight portion of the wall. At a minimum, the straight portion 1700 of the wall needs to be sufficiently high to prevent the ISA coupler 330 from disengaging from the carriage driver 320 when driven in the reverse direction from the direction for engagement.

Figure 18A:
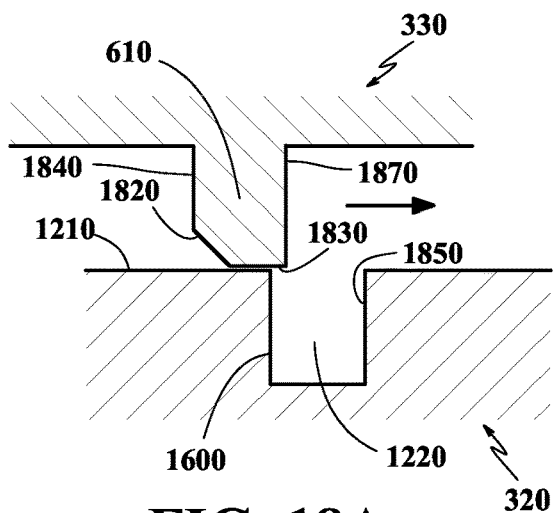
FIG. 18A is an illustration of an exemplary embodiment of an ISA bottom engagement feature that includes an entry ramp approaching a carriage engagement feature.

Referring to FIG. 18A, an exemplary illustration of an ISA bottom boss 1810 that includes an entry ramp 1820 approaching a carriage pocket 1220 is illustrated. It is seen in FIG. 18A that a trailing ISA boss wall 1840 wall includes an entry ramp 1820 that forms an obtuse angle of more than 90 degrees in relation to the lower surface 1830 of the ISA bottom boss 1810, the lower surface supporting the ISA coupler 330 on the surface 1210 of the carriage disk 320 before it engages the carriage pocket 1221.

Figure 18B:
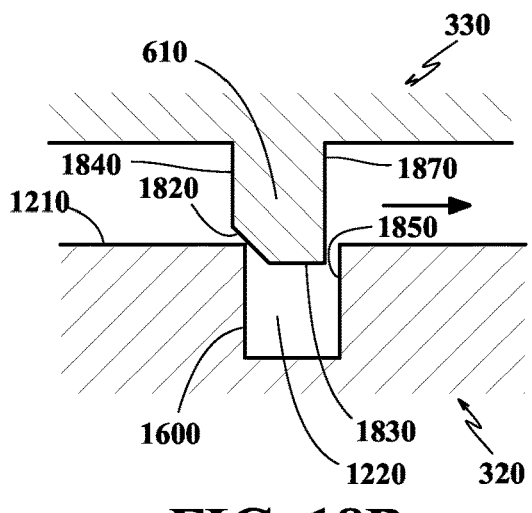
FIG. 18B is an illustration of the exemplary embodiment of FIG. 16A showing the ISA bottom engagement feature approaching the carriage engagement feature and using the entry ramp to begin mating with the carriage engagement feature.

Referring to FIG. 18B, an exemplary illustration of the ISA bottom boss 1810 approaching the carriage pocket 1220 and using the entry ramp 1820 to begin insertion into the carriage pocket 1220. When the ISA bottom boss 1810 approaches the carriage pocket 1220, the entry ramp 1820 allows the ISA bottom boss 1810 to begin insertion into the carriage pocket 1220 before the leading ISA boss wall 1870 reaches the trailing pocket wall 1850. As the ISA coupler 330 continues to rotate, the leading ISA boss wall 1870 comes in contact with the trailing pocket wall 1850 and the ISA bottom boss 1810 is prevented from bypassing the carriage pocket 1220. The spring-loaded mechanism of the carriage driver 320 is then able to propel the insertion of the ISA bottom boss 610 into the carriage pocket 1220. As suggested by FIG. 17B, if the carriage driver 320 contains a spring-loaded mechanism, the carriage driver 320 will rise from the carriage to cause the ISA bottom boss 1810 to enter the carriage pocket 1220.

The angle of the entry ramp 1820 in relation to the lower surface 1830 of the ISA bottom boss 1810 shown is only one exemplary embodiment. The angle of the entry ramp may be more than or less than the angle shown. However, the entry ramp 1820 will always form an obtuse angle with the lower surface 1830 of the ISA bottom boss 1810. It will be appreciated that the entry ramp 1820 should be configured so that the straight portion of the trailing ISA boss wall 1840 wall provides an adequate bearing surface to support the ISA bottom boss 610 when driven against the straight portion of the wall. At a minimum, the straight portion of the trailing ISA boss wall 1840 needs to be sufficiently high to prevent the ISA coupler 330 from disengaging from the carriage driver 320 when driven in the reverse direction from the direction for engagement While certain exemplary embodiments have been described and shown in the accompanying drawings, it is to be understood that such embodiments are merely illustrative of and not restrictive on the broad invention, and that this invention is not limited to the specific constructions and arrangements shown and described, since various other modifications may occur to those of ordinary skill in the art. The description is thus to be regarded as illustrative instead of limiting.

What is claimed is:

1. A sterile adapter for coupling a surgical instrument and a surgical instrument manipulator, the sterile adapter comprising:
   a bottom component including a bottom component opening with a bottom lip having a locking mechanism; and
   a coupling component rotatably coupled to the bottom component, the coupling component including an engagement feature that engages the surgical instrument manipulator, the coupling component further including a locking mechanism opening that engages the locking mechanism when the engagement feature is not engaged with the surgical instrument manipulator.

2. The sterile adapter of claim 1, wherein the locking mechanism is configured as a boss.

3. The sterile adapter of claim 1, wherein the locking mechanism is configured as a ratchet and permits the coupling component to rotate in only one direction when the locking mechanism opening engages the locking mechanism.

4. The sterile adapter of claim 1, wherein the bottom lip includes a plurality of locking mechanisms.

5. The sterile adapter of claim 4, wherein the coupling component includes a plurality of locking mechanism openings.

6. The sterile adapter of claim 5, wherein a number of locking mechanisms comprising the plurality of locking mechanisms corresponds to a number of locking mechanism openings comprising the plurality of locking mechanism openings.

7. The sterile adapter of claim 1, wherein the bottom lip further has a keyway, and the coupling component further has a retention tab and a coupler lip, the retention tab aligning with the keyway to allow the coupling component to pass through the bottom component opening, the retention tab and the coupler lip engaging the bottom lip to retain the coupling component in the bottom component opening when the retention tab and the keyway are not aligned.

8. The sterile adapter of claim 1, wherein the engagement feature includes an entry ramp.

9. A method for coupling a sterile adapter and a surgical instrument manipulator, the method comprising:
   coupling the sterile adapter to the surgical instrument manipulator such that an engagement feature on a rotatable coupling component of the sterile adapter does not engage a rotatable carriage driver on the surgical instrument manipulator which causes a locking mechanism opening on the rotatable coupling component to engage a locking mechanism on the sterile adapter that prevents the rotatable coupling component from rotating; and
   rotating the rotatable carriage driver on the surgical instrument manipulator to cause the rotatable coupling component on the sterile adapter to engage the rotatable carriage driver.

10. The method of claim 9, further comprising rotating the rotatable carriage driver on the surgical instrument manipulator to cause the rotatable coupling component on the sterile adapter to engage the locking mechanism on the sterile adapter.

11. The method of claim 9, wherein the locking mechanism permits the rotatable coupling component to rotate in only a first direction when the locking mechanism opening engages the locking mechanism, and the method further comprises rotating the rotatable carriage driver on the surgical instrument manipulator is a second direction opposite the first direction.

12. The method of claim 9, wherein the carriage driver further includes a carriage pocket having an entry ramp, and the method further comprises rotating the carriage driver in a first direction leading with the entry ramp to cause an engagement feature on the rotatable coupling component to slide down the entry ramp and enter the carriage pocket.

* * * * *